(12) United States Patent
Khare et al.

(10) Patent No.: US 7,888,081 B2
(45) Date of Patent: *Feb. 15, 2011

(54) METHODS AND SYSTEMS FOR INCREASING PRODUCTION OF EQUILIBRIUM REACTIONS

(75) Inventors: Anil Bhagwan Khare, Crystal, MN (US); Brent H. Hilbert, South Haven, MN (US); Christopher Solheid, Minneapolis, MN (US); Sara C. McFarlan, St. Paul, MN (US); Fernando A. Sanchez-Riera, Eden Prairie, MN (US); Kent Floy, Minnetonka, MN (US); Paula M. Hicks, Bend, OR (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/752,492

(22) Filed: May 23, 2007

(65) Prior Publication Data

US 2008/0015361 A1 Jan. 17, 2008

Related U.S. Application Data

(60) Provisional application No. 60/803,105, filed on May 24, 2006.

(51) Int. Cl.
*C12P 13/22* (2006.01)
*C12N 1/21* (2006.01)

(52) U.S. Cl. .................. 435/121; 435/108; 435/193; 435/232; 435/252.3

(58) Field of Classification Search ............... 435/108, 435/193, 232, 252.3, 121
See application file for complete search history.

(56) References Cited

U.S. PATENT DOCUMENTS

| | | | |
|---|---|---|---|
| 3,002,889 | A | 10/1961 | Kinoshita et al. |
| 3,751,458 | A | 8/1973 | Wiley |
| 4,010,204 | A | 3/1977 | Koster et al. |
| 4,975,298 | A | 12/1990 | Van Wyk et al. |
| 5,128,164 | A | 7/1992 | Van Wyk et al. |
| 5,128,482 | A | 7/1992 | Olivier et al. |
| 5,728,555 | A | 3/1998 | Fotheringham et al. |
| 5,994,559 | A | 11/1999 | Abushanab et al. |
| 6,264,999 | B1 | 7/2001 | Yatka et al. |
| 6,846,654 | B1 | 1/2005 | Blackburn et al. |
| 7,064,219 | B2 | 6/2006 | Kawahara et al. |
| 2003/0228403 | A1 | 12/2003 | Amino et al. |
| 2004/0063175 | A1 | 4/2004 | Abraham et al. |
| 2005/0004394 | A1 | 1/2005 | Kawahara et al. |
| 2005/0009153 | A1 | 1/2005 | Sugiyama et al. |
| 2005/0020508 | A1 | 1/2005 | Amino et al. |
| 2005/0106305 | A1 | 5/2005 | Abraham et al. |
| 2005/0112260 | A1 | 5/2005 | Abraham et al. |
| 2005/0118317 | A1 | 6/2005 | Amino et al. |
| 2005/0137246 | A1 | 6/2005 | Amino et al. |
| 2005/0153405 | A1 | 7/2005 | Sugiyama et al. |
| 2005/0170041 | A1 | 8/2005 | Abraham et al. |
| 2005/0221453 | A1 | 10/2005 | Takagi et al. |
| 2005/0221455 | A1 | 10/2005 | McFarlan et al. |
| 2005/0244937 | A1 | 11/2005 | Abraham et al. |
| 2005/0244939 | A1 | 11/2005 | Sugiyama et al. |
| 2005/0272939 | A1 | 12/2005 | Amino et al. |
| 2005/0282260 | A1 | 12/2005 | Hicks et al. |
| 2006/0003411 | A1 | 1/2006 | Sugiyama et al. |
| 2006/0003426 | A1 | 1/2006 | Sugiyama et al. |
| 2006/0009394 | A1 | 1/2006 | Amino |
| 2006/0014819 | A1 | 1/2006 | Mori et al. |
| 2006/0074249 | A1 | 4/2006 | Kawahara et al. |
| 2006/0083695 | A1 | 4/2006 | Mori |
| 2006/0154343 | A1 | 7/2006 | Mori et al. |
| 2006/0172396 | A1 | 8/2006 | Sugiyama et al. |
| 2006/0252135 | A1 | 11/2006 | Brazeau et al. |
| 2007/0099277 | A1 | 5/2007 | Anderson et al. |
| 2007/0105938 | A1 | 5/2007 | Anderson et al. |
| 2008/0020434 | A1 | 1/2008 | Brazeau et al. |

(Continued)

FOREIGN PATENT DOCUMENTS

EP        0 438 314        4/1994

(Continued)

OTHER PUBLICATIONS

Ackerman, "Structure elucidation of and synthetic approaches to monatin, a metabolite from schlerochiton ilicifolius," PhD dissertation, University of Stellenbosch, Jul. 1990.

(Continued)

*Primary Examiner*—Tekchand Saidha

(57) ABSTRACT

Methods and systems for increasing the production of equilibrium reactions are described. In some embodiments, a method comprises removing enzymes from a reaction mixture once equilibrium is achieved, selectively re-adding enzymes and reactants for driving the product-forming reaction to product, and optionally recycling stabilized intermediates, by-products and/or co-products back into the reaction mixture. In some embodiments, a method comprises purifying the desired product from a reaction mixture and selectively recycling one or more components of the reaction mixture, such as original reactants, intermediates, co-products or by-products back into the reaction mixture as desired to improve titer. Systems for implementing the methods are also provided. In some embodiments the methods and systems are implemented for increasing the production of monatin and monatin derivatives, produced in multi-step equilibrium pathways.

3 Claims, 7 Drawing Sheets

U.S. PATENT DOCUMENTS

2008/0020435 A1   1/2008   Burke et al.

FOREIGN PATENT DOCUMENTS

| | | |
|---|---|---|
| EP | 1 045 029 | 10/2000 |
| EP | 1 350 791 | 10/2003 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 719 758 | 11/2006 |
| JP | 2002-060382 | 2/2002 |
| JP | 2003-171365 | 6/2003 |
| JP | 2004-222657 | 8/2004 |
| JP | 2004-331644 | 11/2004 |
| JP | 2004-331650 | 11/2004 |
| WO | WO 89/11212 | 11/1989 |
| WO | WO 03/045914 | 6/2003 |
| WO | WO 03/056026 | 7/2003 |
| WO | WO 03/059865 | 7/2003 |
| WO | WO 03/091396 | 11/2003 |
| WO | WO 2005/001105 | 1/2005 |
| WO | WO 2005/014839 | 2/2005 |
| WO | WO 2005/016022 | 2/2005 |
| WO | WO 2005/020721 | 3/2005 |
| WO | WO 2005/042756 | 5/2005 |
| WO | WO 2005/082850 | 9/2005 |
| WO | WO 2006/011613 | 2/2006 |
| WO | WO 2006/066072 | 6/2006 |
| WO | WO 2006/113897 | 10/2006 |
| WO | WO 2006/116487 | 11/2006 |
| WO | WO 2007/103389 | 9/2007 |
| WO | WO 2007/133183 | 11/2007 |
| WO | WO 2007/133184 | 11/2007 |

OTHER PUBLICATIONS

Ager et al., "Commercial, Synthetic Nonnutritive Sweeteners," *Agnew. Chem. Int. Ed.*, 1998, 37:1802-1817.

Ager et al., "Novel biosynthetic routes to non-proteinogenic amino acids as chiral pharmaceutical intermediates," *Journal of Molecular Catalysis B: Enzymatic*, 2001, 11:199-205.

Azuma et al., "Hyper-production of L-tryptophan via fermentation with crystallization," *Appl. Microbiol. Biotechnol.*, 1993, 39:471-476.

Bae et al., "Production of aromatic D-amino acids from α-keto acids and ammonia by coupling of four enzyme reactions," *Journal of Molecular Catalysis B: Enzymatic*, 1999, 6:241-247.

Bassoli, "'Chemistry-Nature,' still an open match for the discovery of new intensive sweeteners," *Agro FOOD industry hi-tech*, 2004, 15(4):27-29.

Bassoli et al., "Design and synthesis of new monatin derivatives," *Abstracts, 13th. International Symposium on Olfaction and Taste (ISOT XIII), 14th European Chemoreception Research Organization Congress (ECRO XIV)*, Jul. 20-24, 2000, p. 162.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [translated by Google], Jan. 2003, Universidade Estadual de Campinas Instituto de Quimica, Dissertation of Masters.

DeLuna et al., "NADP-Glutamate Dehydrogenase Isoenzymes of *Saccharomyces cerevisiae*: Purification, Kinetic Properties, and Physiological Roles," *J. Biol. Chem.*, 2001, 276:43775-43783.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetener," *Synthetic Communications*, 1993, 23(18):2511-2526.

Izumi, "Introduction," *Synthetic Production and Utilization of Amino Acids*, 1974, Kankeko et al. (eds.), Halstad Press, Chapter 1, pp. 3-16.

Juhl et al., "Catalytic asymmetric homo-aldol reaction of pyruvate—a chiral Lewis acid catalyst that mimics aldolase enzymes," *Chem. Commun.*, 2000, 2211-2212.

Kogiso et al., "Control of Lactamization during the Synthesis of the Monatin Analogue," *Peptide Science*, 2003, pp. 195-198.

Li et al., "Nonproteinogenic alpha-Amino Acid Preparation Using Equilibrium Shifted Transamination," *Organic Process Research & Development*, 2002, 6:533-538.

Nakamura et al., "Total Synthesis of Monatin," *Organic Letters*, 2000, 2(19):2967-2970.

Nakamura et al., "Total Synthesis of Monatin and the Taste Experience," *Peptide Science*, 2003, pp. 61-64.

Oliveira et al., "Highly diastereoselective alkylation of a pyroglutamate derivative with an electrophile obtained from indole. Synthesis of a potential intermediate for the preparation of the natural sweetener (−)-monatin," *Synthetic Communications*, 2000, 30(12):2143-2159.

Oliveira et al., "Diastereoselective formation of a quaternary center in a pyroglutamate derivative. Formal synthesis of Monatin," *Tetrahedron Letters*, 2001,42:6793-6796.

Tamura et al., "Highly stereoselective synthesis of (−)-monatin, a high-intensity sweetener, using chelation-controlled nitron cycloaddition," *Chemical Communications*, 2003, 21:2678-2679.

Tamura et al., "Stereoselective Synthesis of 4-Hydroxy 4-Substituted Glutamic Acids," *J. Org. Chem.*, 2005, 70(12):4569-77.

Vleggaar et al., "Structure elucidation of monatin, a high-intensity sweetener isolated from the plant *Schlerochiton ilicifolius*," *J. Chem. Soc. Perkin Transactions 1: Organic and Bio-Organic Chemistry* (1972-1999), 1992, 22:3095-3098.

Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.

Eggeling and Sahm, "Amino-acid production: principles of metabolic engineering," *Metabolic Engineering*, 1999, Lee & Papoutsakis eds., Marcel Dekker, Inc., New York.

Guo et al., "Protein tolerance to random amino acid charge," *Proc. Natl. Acad. Sci. USA*, 2004, 101(25):9205-9210.

Seffernick et al., "Melamine deaminase and atrazine chlorohydrolase: 98 percent identical but functionally different," *J. Bacteriology*, 2001, 183(8):2405-2410.

Seo Jeong-Sun et al., "The genome sequence of the ethanologenic bacterium *Zymomonas mobilis* ZM4," *Nature Biotechnology*, 2005, 23(1):63-68.

Whisstock et al., "Prediction of protein function from protein sequence," *Q. Rev. Biophysics*, 2003, 36(3):307-340.

Witkowski et al., "Conversion of b-ketoacyl synthase to a malonyl decarboxylase by replacement of the active-site cysteine with glutamine," *Biochemistry*, 1999, 38:11643-11650.

GenBank Accession No. CAC46344 dated Aug. 16, 2005, 2 pages.

Gramatikova et al., "Pyridoxal 5'-phosphate-dependent catalytic antibody," *J. Biol. Chem.*, 1996, 271:30583-30586.

Inagaki et al., "Purification and Characterization of Amino Acid Racemase with Very Broad Substrate Specificity from *Aeromonas caviae*," *Agric. Biol. Chem.*, 1987, 51(1):173-180.

Kino et al., "Synthesis of DL-tryptophan by modified broad specificity amino acid racemase from *Pseudomonas putida* IFO 12996," *Appl. Microbiol. Biotechnol.*, 2007, 73(6):1299-1305.

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Science*, 1995, 4:1750-1757.

Mateo et al., "Epoxy Sepabeads: A Novel Epoxy Support for Stabilization of Industrial Enzymes via Very Intense Multipoint Covalent Attachment," *Biotechnol. Prog.*, 2002, 18(3):629-634.

Wagner et al., "Efficient Aldolase Catalytic Antibodies That Use the Enamine Mechanism of Natural Enzymes," *Science*, 1995, 270:1797-1800.

Zhong et al., "Broadening the Aldolase Catalytic Antibody Repertoire by Combining Reactive Immunization and Transition State Theory: New Enantio- and Diastereoselectivities," *Angew Chem. Int. Ed.*, 1999, 39(24):3738-3741.

SEQUENCE LISTING

<160> NUMBER OF SEQ ID NOS: 4

<210> SEQ ID NO 1
<211> LENGTH: 690
<212> TYPE: DNA
<213> ORGANISM: Bacillus subtilis

<400> SEQUENCE: 1

```
atgcctatcg ttgttacgaa gatcgaccga cccagcgcgg cggacgtcga aaggatcgcc      60
gcctatggtg tcgcgacctt gcatgaagcg caaggacgaa ccgggttgat ggcgtccaat     120
atgcgcccaa tctatcgccc tgcgcacatt gccgggcccg cggtgacctg ccttgtggcg     180
cctggcgaca attggatgat ccatgtcgcc gtcaacagt gccagccggg agatgtcctg      240
gtcgtggtac cgaccagccc ctgcgaagac ggctatttcg gcgatctgct ggcgacctcg     300
ctgcggtcgc gcggggtcaa aggtctgatc atcgaggccg gcgtacgcga tatcgcgaca     360
ttgaccgaga tgaaattccc ggtctggtcc aaggcggtgt tcgcgcaagg aacggtcaag     420
gagaccatcg ccagcgtcaa tgtgcccctc gtctgcgcgg gcgcccgcat cgtgccgggc     480
gatctgatcg ttgccgacga cgacggggtc gtcgtgattc caagacgttc cgttccggcg     540
gtcctttcca gcgccgaggc ccgcgaagag aaggaagccc gcaaccgcgc ccgcttcgaa     600
gctggcgagc tgggcctcga cgtctacaac atgcgccagc gcctggccga caagggcttg     660
cgctatgtcg agcggctgcc cgaggaatag                                      690
```

<210> SEQ ID NO 2

```
<211> LENGTH: 229
<212> TYPE: PRT
<213> ORGANISM: Bacillus subtilis

<400> SEQUENCE: 2

Met Pro Ile Val Val Thr Lys Ile Asp Arg Pro Ser Ala Ala Asp Val
 1               5                  10                  15

Glu Arg Ile Ala Ala Tyr Gly Val Ala Thr Leu His Glu Ala Gln Gly
                20                  25                  30

Arg Thr Gly Leu Met Ala Ser Asn Met Arg Pro Ile Tyr Arg Pro Ala
            35                  40                  45

His Ile Ala Gly Pro Ala Val Thr Cys Leu Val Ala Pro Gly Asp Asn
 50                  55                  60

Trp Met Ile His Val Ala Val Glu Gln Cys Gln Pro Gly Asp Val Leu
 65                  70                  75                  80

Val Val Val Pro Thr Ser Pro Cys Glu Asp Gly Tyr Phe Gly Asp Leu
                85                  90                  95

Leu Ala Thr Ser Leu Arg Ser Arg Gly Val Lys Gly Leu Ile Ile Glu
                100                 105                 110

Ala Gly Val Arg Asp Ile Ala Thr Leu Thr Glu Met Lys Phe Pro Val
            115                 120                 125

Trp Ser Lys Ala Val Phe Ala Gln Gly Thr Val Lys Glu Thr Ile Ala
130                 135                 140

Ser Val Asn Val Pro Leu Val Cys Ala Gly Ala Arg Ile Val Pro Gly
145                 150                 155                 160

Asp Leu Ile Val Ala Asp Asp Gly Val Val Ile Pro Arg Arg
                165                 170                 175

Ser Val Pro Ala Val Leu Ser Ser Ala Glu Ala Arg Glu Glu Lys Glu
                180                 185                 190

Ala Arg Asn Arg Ala Arg Phe Glu Ala Gly Glu Leu Gly Leu Asp Val
            195                 200                 205

Tyr Asn Met Arg Gln Arg Leu Ala Asp Lys Gly Leu Arg Tyr Val Glu
210                 215                 220

Arg Leu Pro Glu Glu
225

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3
ataagacata tgcctatcgt tgttacgaag                                        30

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide

<400> SEQUENCE: 4
ataagaggat ccttattcct cgggcagccg ctc                                    33
```

METHODS AND SYSTEMS FOR INCREASING PRODUCTION OF EQUILIBRIUM REACTIONS

CLAIM OF PRIORITY

This application claims priority to U.S. Provisional Application Ser. No. 60/803,105, filed on May 24, 2006, the entire contents of which are hereby incorporated by reference.

BACKGROUND

1. Field of the Invention

The present invention is directed to methods and systems for increasing the production of a desired product of multi-step step pathway involving equilibrium reactions. In some embodiments, the desired product is the high intensity sweetener, monatin.

2. Background

Monatin is a high-intensity sweetener having the chemical formula:

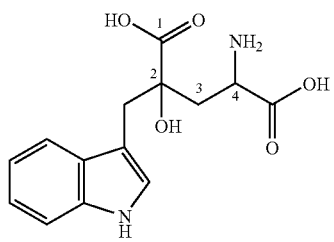

Because of various naming conventions, monatin is also known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

Monatin includes two chiral centers leading to four potential stereoisomeric configurations. The R,R configuration (the "R,R stereoisomer" or "R,R monatin"); the S,S configuration (the "S,S stereoisomer" or "S,S monatin"); the R,S configuration (the "R,S stereoisomer" or "R,S monatin"); and the S,R configuration (the "S,R stereoisomer" or "S,R monatin").

WO 2003/091396 A2, which is hereby incorporated by reference, discloses, inter alia, polypeptides, pathways, and microorganisms for in vivo and in vitro production of monatin. WO 2003/091396 A2 (see, e.g., FIGS. 1-3 and 11-13), and U.S. Patent Publication No. 2005/282260 describe the production of monatin from tryptophan through multi-step pathways involving biological conversions with polypeptides (proteins) or enzymes. One pathway described involves converting tryptophan to indole-3-pyruvate ("I-3-P") (reaction (1)), converting indole-3-pyruvate to 2-hydroxy 2-(indol-3-ylmethyl)-4-keto glutaric acid (monatin precursor, "MP") (reaction (2)), and converting MP to monatin (reaction (3)), biologically, for example, with enzymes.

Certain isomeric forms of monatin can be found in the bark of roots of the *Schlerochiton ilicifolius* plant located in the Transvaal Region of South Africa. However, the concentration of the monatin present in the dried bark, expressed as the indole in its acid form, has been found to be about 0.007% by mass. See U.S. Pat. No. 4,975,298. The exact method by which monatin is produced in the plant is presently unknown.

At least in part because of its sweetening characteristic, it is desirable to have an economic source of monatin. Thus, there is a continuing need to increase the efficiency of synthetic pathways, such as monatin synthetic pathways, including the biological multi-step pathways described above.

SUMMARY

Methods and systems for synthesizing a desired ultimate end product by a biological synthetic pathway are provided. According to an embodiment, carbon trapped in the form of at least one pathway intermediate that would otherwise be lost at the conclusion of the synthetic pathway is rescued and converted into the desired end product by altering the original pathway in a manner that converts such carbon into the desired ultimate end product. A person of ordinary skill should understand that the term "carbon" is used herein as shorthand for the relevant compound. That is, the statement "carbon is converted into the desired product" means that the carbon-containing compound is converted into the desired product.

In an embodiment, intermediates and unreacted components are recycled for re-use, reducing waste and improving the carbon yield of product. That is, this net removal of product can perturb the equilibrium and can result in more product generation for a given quantity of original reactants than without product removal. This can improve the economics of production.

In another embodiment of the invention, one or more components of the reaction mixture may be recycled to improve production above the equilibrium production amount. That is, where a series of reactions is performed to produced a desired product, unwanted side reactions, some of which may be irreversible, others of which may be reversible, may also occur. Where the side reactions are irreversible, or essentially irreversible, the carbon utilized in those side reactions can be unrecoverable for the desired pathway. Stated otherwise, if the irreversible side reactions are not controlled, they may ultimately overtake the speed of the desired reactions. The more labile intermediates and byproducts, therefore, can be stabilized to prevent degradation. Thus, in an embodiment of the invention, the labile or unstable intermediates and side products are stabilized by conversion to more stable components that can be recycled back into the mix of original reactants. Conversion of unstable intermediates to product or more stable compounds can result in further conservation of carbon and improved product yields. Where the side reactions are reversible, the product of the reversible side reactions can be recycled back into the mix of original reactants to prevent or alleviate additional original reactants from being lost to undesired byproduct production. By adding in, for example, equilibrium amounts of the unwanted side products with the original reactants, the net result is that the unwanted side reactions do not proceed forward.

In a particular embodiment, monatin is produced from tryptophan by converting tryptophan to indole-3-pyruvate ("I3P"), reacting I3P with pyruvate to form alpha-keto acid monatin ("MP"), and then reacting MP to form monatin, wherein each of the reactions is facilitated by one or more enzymes. Competitive reactions may also occur, in addition to the reactions along the product-forming pathway. For example, in the identified monatin-production process, pyruvate may also react with itself to form 4-hydroxy-4-methyl-2-oxoglutarate ("HMO"), and HMO may be converted to 4-hydroxy-4-methyl glutamate ("HMG") by the same enzymes that convert tryptophan to I3P. Thus, a method for improving economics involves not only recycling compounds that are directly involved in monatin production, but also recycling byproducts of side reactions. Such recycled byproducts can be converted back into compounds useful for production of monatin.

In an embodiment, less stable compounds are converted to more stable compounds prior to separation and/or recycle. "Less stable" and "more stable" is in reference to the probability for degradation of the compound under the chosen conditions for separation and recycle. In some embodiments wherein monatin is produced, for example from tryptophan, the alpha-keto acid intermediates are converted to corresponding amino acids prior to separation and recycle. In a particular embodiment, where monatin is made by the above-described pathway, conversion of less stable to more stable compounds can be achieved by first allowing the monatin production reaction to proceed to equilibrium, next removing enzymes involved in the monatin production pathway, then re-adding one or more enzymes which facilitate the MP conversion and the tryptophan conversion along with additional alanine. Selectively adding appropriate enzymes plus alanine loading can cause the less stable MP to form additional, more stable monatin, and the less stable I3P to be converted into more stable tryptophan, which trypotophan can then be recycled for further monatin production.

Accordingly, in one embodiment, the method of the invention proceeds in several stages. In the first stage, the synthetic pathway encompasses conversion of an initial substrate X into one or more intermediates in the pathway, (Y1-Yn; where Y1 is converted into intermediate Y2, which is converted into intermediate Y3, etc., until the last intermediate, intermediate Yn, is produced). Intermediate Yn is then converted into the product Z. The conversions of X into Y1-Yn and then into Z can take place, in a single mixture or composition, generally, at least in part, simultaneously. In the second stage, at a desired time after initiating the first stage, at least one, or all of the molecular entities that facilitated the enzymatic or chemical reactions (i.e., that convert X into Y1, Y1 into Y2, Y2 into Y3, and so on until Y(n−1) is converted to Yn, and then Yn into Z) in the first stage are removed from the reaction mixture, or are otherwise inhibited, degraded or inactivated, or made incapable of functioning. In the third stage, at least one intermediate Y that is still present in the mixture after stage 2 is then converted into product Z by the addition or readdition of a molecular entity that is capable of facilitating the conversion of intermediate Yn into product Z.

In a further embodiment, in the third stage, the intermediate Yn is converted into product Z.

In a further embodiment, a synthetic pathway is provided in which product Z is monatin.

In a further embodiment, all of the molecular entities that are responsible for facilitating the reactions of the pathway are removed from the reaction mixture prior to stage 3.

In a further embodiment, only the molecular entity that facilitated the reaction of the intermediate step that is to be eliminated (for example, the reaction that converts Yn−1 to Yn) is removed from the reaction mixture, or is otherwise inhibited, degraded or inactivated.

In a further embodiment, more than one of the molecular entities that are capable of facilitating the one or more reactions in the pathways are added back to the mixture in stage 3.

In certain embodiments, the use of the method provided herein can improve the overall amount, or titer, of the product of a multi-step equilibrium process over the equilibrium process alone. For example, the concentration, or titer, of a product may be improved by 1.7 times, or in certain cases, the concentration, or titer, may be improved by 2 times. The molar yield of the product from a given substrate (moles of product produced divided by the initial moles of substrate supplied) may be improved 1.7 times, or in certain cases, 2 times. The overall carbon yield (amount of carbon contained in product divided by amount of carbon contained in substrates provided) can also be improved over the equilibrium process alone, if substrates, particularly the additional substrates added in stage 3, are recycled.

The invention further embodies systems for the production of monatin that utilize the methods of the invention, and an apparatus for such production. In some embodiments, a method for making monatin in a multi-step pathway involves allowing a first composition comprising one or more reactants and one or more facilitators to react to form monatin and one or more intermediates in the monatin-production pathway. The first composition is allowed to react for a specified time period, for example until equilibrium is reached. After the specified time period, one or more of the facilitators is removed, inhibited, inactivated, or degraded, whereby the production of monatin in the pathway is increased by then adding a facilitator to the composition that is involved in the reaction step producing monatin, or by uninhibiting or reactivating the facilitator(s) involved in the reaction step producing monatin. In some embodiments, in addition to adding, uninhibiting, or reactivating the appropriate facilitators, additional compounds are added to the composition that participate in driving the monatin-producing step toward production of monatin.

In some embodiments, the method of producing monatin involves producing monatin in a pathway having at least two, or at least three reaction steps, wherein one of the reaction steps produces monatin and another of the reaction steps is limiting the amount of monatin pathway intermediate available to the monatin-producing reaction step, compromising at least the limiting step of the pathway after a desired time period, for example after the pathway reaches equilibrium, followed by loading a component for example a facilitator, a reactant, or both, back into the pathway to push the monatin-producing step toward production of monatin. "Compromising a reaction" means disrupting a reaction so that it cannot occur or reducing the efficiency of the reaction.

This summary is not intended to act as a limitation on the scope of the appended claims.

DESCRIPTION

Figure 1:
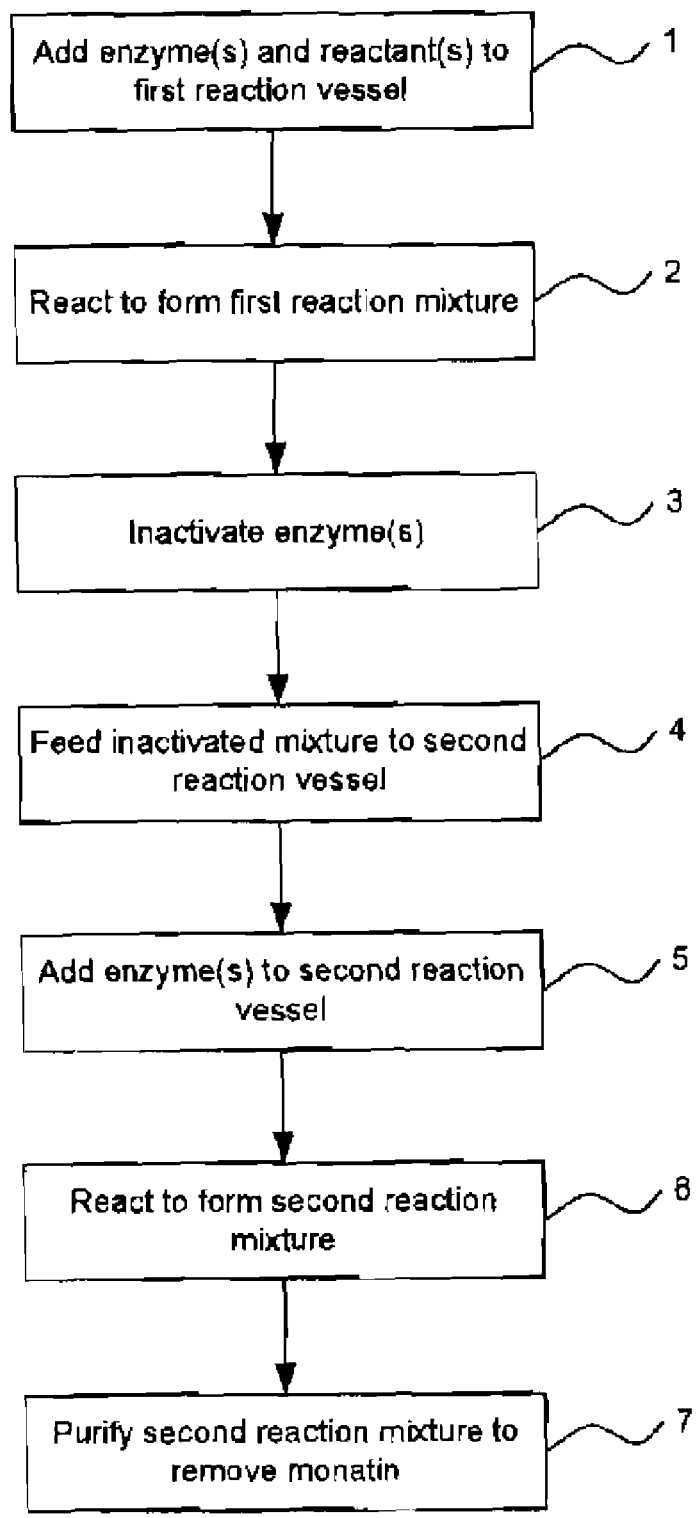
FIG. 1 is a process flow chart that exemplifies production of monatin in accordance with an embodiment of the invention.

As used herein, "including" means "comprising", and "includes" means "includes but is not limited to" unless otherwise clear from context. As used herein, the phrases "for example" or "such as" are non-limiting and mean "for example but not limited to" and "such as but not limited to." In addition the singular forms of "a" or "an" or "the" include plural references unless the context clearly dictates otherwise. For example, reference to "comprising an enzyme" means including one or more enzymes. The term "abouc" encompasses the range of experimental error that occurs in any measurement. Unless otherwise stated, all measurement numbers are presumed to have the word "abouc" in front of them even if the word "about" is not expressly used.

As used herein, the terms "separating" and "removing" are used interchangeably. Thus, for example, separating monatin from a composition, is the same as removing monatin from a composition. A person of ordinary skill would understand that separating and removing do not require complete separation and removal, but rather that for example, in some separations such as with membrane filtrations only gross separations are achieved because there may be some bleed through of desired components into undesired components. Thus "separating" and "removing" means only that the desired component, when separated, is more pure than prior to separation or removal.

As used herein, unless otherwise indicated, the term "monatin," is not limited to any specific stereoisomeric form of monatin.

Assaying "monatin" encompasses assaying a composition for the presence of monatin. Unless otherwise indicated, the monatin in a monatin composition is not limited to any specific stereoisomeric form. Therefore, a composition that includes "monatin," unless otherwise indicated, includes and encompasses compositions that contain any or all of the four stereoisomers of monatin, for example, compositions that contain all four stereoisomers of monatin, compositions that contain any combination of monatin stereoisomers, (e.g., a composition including only the R,R and S,S, stereoisomers of monatin), and, compositions that contain only a single isomeric form of monatin.

Wherever chemical names are identified in the specification and claims (e.g., "monatin" or "monatin precursor"), the term "and/or salts thereof" should be understood to be included unless otherwise indicated. For example, the phrase "indole-3-pyruvate is converted to monatin precursor" should be understood to read "indole-3-pyruvate and/or salts thereof is converted to monatin precursor and/or salts thereof." A person of ordinary skill would appreciate that under the various exemplified reaction conditions, the salts of the named compounds, including the named reactants, substrates, intermediates and products in the monatin synthetic reactions, are in fact present or may be present.

The terms "polypeptide" and "protein" are used interchangeably. The term "polypeptide," unless otherwise clear from the context, is not limited to a single polypeptide chain but includes multimers of chains (for example, homologous or heterologous dimers, trimers, tetramers, etc.), if such multimeric forms are necessary to facilitate, for example, to catalyze, a reaction in which the polypeptide participates.

A "biological conversion" is a conversion of a compound (the substrate), to a different compound (the product), that is facilitated by, a for example, polypeptides and other facilitators described in the following paragraph. Biological conversions include enzymatic reactions in which an enzyme facilitates (catalyzes) the conversion of one or more substrates into one or more products. A "biological synthesis" or "biosynthesis" is a synthesis involving at least one biological conversion.

The description herein exemplifies enzymes as examples of polypeptides that can be used to facilitate reactions in biological synthesis pathways, for example, the exemplified synthesis pathways for monatin synthesis. However, it is to be understood that other molecular entities may be used as facilitators to perform a desired reaction, including catalytic antibodies, and facilitators having an RNA component, such as, for example, catalytic RNA, or ribozymes. A catalytic antibody having aldolase activity is commercially available (Aldolase antibody 38C2, Aldrich catalog nos. 47,995-0 and 48,157-2). Preparation of catalytic antibodies having aldolase activity are described in Wagner, J. et al., *Science* 15: 1797-1800 (1995) and Zhong, G. et al., *Angew Chem. Int. Ed. Engl.* 16: 3738-3741 (1999) and catalytic antibodies having transaminase activity are described in Gramatikova, S. I. et al., *J. Biol. Chem.* 271: 30583-30586 (1996). Further the use of catalytic antibodies to catalyze reactions is discussed in U.S. Pat. No. 6,846,654.

A multi-step pathway is a series of reactions that are linked to each other such that subsequent reactions utilize at least one product of an earlier reaction. For example, in such a pathway, the substrate(s) of the first reaction is converted into one or more products, and at least one of those products can be utilized as a substrate(s) for the second reaction. The second reaction then also produces one or more products, and at least one of those products can be utilized as a substrate(s) for a third reaction, and so forth. In a multi-step pathway, one, some, or all of the reactions in the pathway can be enzymatically catalyzed, or otherwise facilitated by a macromolecular entity such as a catalytic antibody or catalytic RNA. One, some or all of the reactions in the pathway can be reversible. A biological synthesis is a synthesis involving at least one reaction step that is enzymatically catalyzed, or otherwise facilitated by a macromolecular entity such as a catalytic antibody or catalytic RNA. A multi-step equilibrium pathway is a multi-step pathway in which at least one of the reactions (i.e. steps) in the pathway is an equilibrium or reversible reaction.

According to embodiments of the invention, one or more of the reactions in a synthetic pathway, such as a monatin synthetic pathway, is altered, after such synthetic pathway has initiated synthesis of the product (exemplified by the product, monatin). The pathway is altered or "broken" by removing at least one of the facilitators or otherwise compromising the pathway, for example by preventing that facilitator from functioning, or lessening the ability of that facilitator to perform its function. For example, the pathway may be altered or "broken" by removing, inhibiting, or destroying an enzyme that facilitates a specific intermediate reaction in the pathway. Alteration of the pathway can also include changing the reaction conditions so that what was previously a reversible reaction becomes an irreversible reaction, or at least shifting the equilibrium of such reaction, for example, to the right, toward the synthesis of a desired product, for example, toward monatin synthesis, but preferably in a manner that does not result in recreation of the original pathway. As can be understood from the examples herein, recreation of the original pathway (or similar terms such as regeneration of the original pathway) means reactivation of all steps in the original pathway.

In an embodiment, the alteration results in a pathway that has a greatly diminished ability to synthesize, or, can no longer synthesize, the desired, ultimate end product, for example monatin, when the only substrates supplied are those for the first reaction in the pathway. The alteration preferably detectably lessens, or stops, synthesis of the end product through the complete pathway. Because the alteration occurs after product synthesis had been initiated, after the alteration of the pathway, the mixture in which the original reactions were performed contains certain amounts of the various intermediate product(s) of the pathway that were in the mixture at the time the pathway was altered, including the product(s) of the altered, preferably non-functional, reaction.

According to an embodiment of the invention, at least one intermediate product is captured and converted into the desired ultimate end product, for example, monatin, by re-adding one or more appropriate facilitators, for example, one or more enzymes, to the reaction mixture that facilitate the conversion of such intermediate product into the desired end product, for example, monatin or into a precursor of the desired end product, for example, into monatin precursor (MP), but without regenerating, or under conditions that do not regenerate, the original pathway. In an embodiment, the product of the inactivated reaction is separated from the facilitator (for example, from the enzyme) that produced it prior to adding components back to the mixture to facilitate conversion of that intermediate product into the ultimate end product, such as into monatin. In an embodiment, the substrates (for example, reactants, intermediates and product) are separated from the enzymes, the substrates form a second reaction mixture and the enzymes are recycled back to a first reaction mixture. At least an enzyme capable of facilitating the step which generates product (typically the last step of the multi-step pathway) is added or re-introduced into the second mixture. In a further embodiment, other components (for example reactants) which cause the product-producing step to favor production of product are added to the second mixture.

As would be understood by one of ordinary skill in the art, separation of components (such as separation of facilitator(s) from reactant(s)) may not be complete and some portion of the facilitator may remain in the reaction mixture. Similarly, as used herein the term "purification" or similar terms (such as "purified) indicates that contaminants have been removed from the sample of interest but does not require absolute purity. Rather, "purification" is intended as a relative term, unless otherwise indicated by the context. Thus, for example, monatin is purified from a monatin-containing composition where the purified monatin is at a higher concentration relative to contaminants than it was in the monatin-containing composition.

As exemplified in an embodiment of the invention, the reaction materials for the production of a desired ultimate end product, such as monatin, are brought together to form a first mixture. These reaction materials include the appropriate substrate(s), co-factors, enzymes, buffer components, etc., generally, all the necessary components for the pathway reactions for the biological synthesis of the desired ultimate end product, here exemplified by the synthesis of monatin. In the beginning, at least the substrate(s) for the first enzyme in the pathway is present, although other intermediate substrates may be provided if desired.

In this exemplified embodiment, the production of the ultimate end product (the end product that it is desired that the pathway produce, for example, monatin) is allowed to proceed by this pathway for a desired time. The ultimate end product, for example, monatin, can be removed from this mixture as it is produced or the ultimate end product, can be allowed to accumulate in the first mixture, for example until equilibrium is reached. At a desired time, the synthesis of ultimate end product by the above pathway is compromised, such that it is altered or completely stopped by inhibiting or otherwise inactivating, or removing, one or more of the enzymes or facilitators of one or more of the specific reactions. The removal, inactivation or inhibition is such that synthesis of the ultimate end product by the original pathway can no longer proceed, or proceeds only at a relatively lower rate, due to this inhibition, inactivation or removal of the one or more facilitator(s). The reaction performed by the facilitator(s) that is removed, inhibited or inactivated is said to be compromised. A non-limiting example of compromising a reaction includes removing (or separating, which term is used herein interchangeably with removing) the enzyme that facilitates the reaction from the reaction mixture. Another non-limiting example of compromising a reaction includes removing a cofactor necessary for enzyme action from the reaction mixture. In one embodiment, where monatin is produced in a pathway utilizing enzymes that have magnesium or phosphate cofactors, reactions can be compromised by inactivating enzymes through the removal of magnesium or phosphate, for example by using a desalting column.

Any reaction that produces an intermediate compound in the pathway can be the target that is to be compromised. In an embodiment, a reversible reaction that produces an intermediate in the pathway is compromised. In an embodiment, at least the reaction with the lowest or with a low equilibrium constant (e.g. about 1 or less) is compromised. In an embodiment, the reaction that is compromised is at least the next to last reaction in the pathway, however, any one, any subset or all of the reactions that are capable of providing one or more intermediate product(s) in the pathway may be altered or compromised. In some embodiments, the reaction is carried out in a manner that reduces the concentration of unstable intermediates. For example, in certain monatin production pathways, a reaction producing the alpha-carbonyl carboxylate 2-hydroxy-2-(indol-3ylmethyl)-4-ketoglutaric acid is disturbed to reduce the concentration of that intermediates. In certain monatin production pathways, reactions are carried out in such a way to convert the alpha-carbonyl carboxylates indole-3-pyruvate, 4-hydroxy-4-methyl-2-oxoglutarate ("HMO") and 2-hydroxy-2-(indol-3ylmethyl)-4-ketoglutaric acid into their corresponding amino acids by adding increased concentrations of an amino donor to the reactions.

To alter or compromise a desired reaction, for example, a desired intermediate reaction, one or more of the facilitators, for example, one or more enzymes that catalyze reversible intermediate reaction(s) in the pathway, can be removed or inhibited from the composition. This results in a composition that contains, inter alia, the intermediate(s) of the pathway, but not the necessary enzyme(s) to catalyze conversion of the intermediates into the ultimate end product, for example monatin.

After the desired reaction(s) is compromised, for example, its facilitator is removed, inhibited or inactivated, the mixture may be supplemented with a component that will convert one or more of the reaction intermediates into the ultimate end product, for example monatin. The supplemental component is such that the composition maintains the state in which the intermediate reaction is compromised, for example, is missing, inhibited or inactivated so that the initial pathway is not simply recreated in the original active form. By re-establishing a reaction in the "broken" pathway that facilitates the conversion of the intermediate that was the product of the missing facilitator, for example, the product of the missing enzyme into the ultimate end product or a precursor of that product, carbon that was otherwise trapped at that intermediate stage, or downstream therefrom, is recovered into the ultimate end product. Such conversion can re-establish that part of the original pathway from that intermediate product to the ultimate end product, or can establish a different reaction(s) path from the intermediate product to the ultimate end product. Thus, the synthesis of a desired ultimate end product, for example, monatin is made more efficient, and with less loss or waste of intermediates in the pathway. If the additional reactant component(s) added are recycled, this results in a more economical production due to increased yield.

The reaction mixture that results after conversion of the intermediate into the ultimate end product can be used directly for any desired purpose for which it is suitable.

Alternatively, compositions or preparations (liquid or solid) that contain the ultimate end product, for example, monatin, can be further processed by extracting, purifying or isolating the ultimate end product, or compositions containing such end product, for example, monatin, from the first and/or second reaction mixture(s) as desired, using methods known in the art.

In the discussion herein, the mentioning of three stages is not intended to exclude the addition of other stages, but only intended as a tool to facilitate the discussion of the temporal aspects of the method of the invention.

Thus, in one embodiment, the invention can be described as a pathway for synthesis of a compound, for example, monatin, that proceeds in several stages. In the first stage, the pathway encompasses conversion of an initial substrate X into one or more intermediates in the pathway, (Y1-Yn; where intermediate Y1 is converted into intermediate Y2, which is converted into intermediate Y3, etc., until the last intermediate, intermediate Yn is produced). Intermediate Yn is then converted into the product Z, for example, monatin. The conversions of X into Y1-Yn and then into Z can take place, in a single mixture or composition, generally, at least in part, simultaneously. In the second stage, at a desired time after initiating the first stage, the molecular entities that performed or facilitated the enzymatic or chemical reactions (i.e., that convert X into Y1, Y1 into Y2, Y2 into Y3, and so on until Y(n−1) is converted to Yn, and then Yn into Z) in the first stage are removed from the reaction mixture, or are otherwise inhibited, degraded or inactivated, or otherwise compromised so that they are incapable of functioning, or their functioning is greatly diminished. In the third stage, one or more of the intermediates, for example, the intermediate Yn, that is still present in the mixture after stage 2 is then converted into product, for example, monatin, or into an intermediate that can be converted into the product, for example, monatin, by the addition or readdition of a molecular entity (or entities) that is capable of facilitating the conversion of Yn into product, for example, monatin, or into such intermediate.

In a specific embodiment, for example wherein monatin is produced in a multi-step biosynthetic reaction from tryptophan, as described above and elsewhere in this specification, the process can target accumulation of MP. In an embodiment, this can be accomplished by isolating the reaction forming MP from I3P, for example by removing (inhibiting or inactivating) enzymes facilitating other reactions in the pathway, or by removing, inhibiting or inactivating all the enzymes and then re-adding, enabling or reactivating the enzyme(s) that facilitates the I3P to MP conversion, and loading the MP formation reaction with one of the reaction substrates. In an embodiment, the resultant MP is purified from the reaction mix.

Thus, in one embodiment, the synthesis of an ultimate end product, for example, monatin, occurs in three stages. In a first stage, all the components for the synthetic pathway are present in a single mixture, and the ultimate end product, for example, monatin, is allowed to form. In a second stage, all or some of the metabolites, for example, monatin and the chemical intermediates in the monatin synthetic pathway, are separated from the facilitators, the larger macromolecules such as the polypeptides or enzymes that facilitated or catalyzed the various reactions in the pathway, or the activity of one or all these macromolecules is otherwise compromised so as to impede the functioning of such one or all facilitators. In a third stage, new facilitator(s) or, a subset of the original facilitators, for example, a subset of the pathways' enzymes, at least one of which can facilitate only certain desired reaction(s) of the synthetic pathway are added or added back to the metabolite mixture. The new facilitators or this subset preferably contains at least one facilitator, for example, an enzyme, that facilitates the synthesis of the ultimate end product, for example, monatin, itself. However, the new facilitators, or this subset, lacks one or more of the facilitators (for example, lacks one or more enzymes) that facilitate at least one earlier step in the synthetic pathway for the ultimate product, for example, monatin. The addition or readdition of the new facilitator, for example, the final enzyme in the pathway, in the absence of an earlier facilitator, that can utilize that carbon that had been present in the mixture as an intermediate and convert such carbon to the the ultimate product, for example, into monatin, thus increases the overall yield of the pathway conversion.

The methods of the invention in some embodiments are especially useful for synthetic pathways such as monatin synthetic pathways that utilize reversible pathways. Such reversible pathways can result in futile cycles in which carbon intended for product formation is instead diverted into the reverse reaction. Thus, when reversible reactions are used, rather than driving the conversion of the substrate into the product to completion, a certain amount of the product may be reconverted into substrate.

The methods of the invention in some embodiments minimize such carbon loss by converting, in stage 3, precursor that would otherwise have been discarded with other reaction components, or which would have decomposed upon attempted recycling, into the ultimate end product, for example, monatin. In a highly preferred embodiment, an enzyme is added in stage 3 that can catalyze the conversion of the immediate precursor of the end product into the ultimate end product, for example, that converts monatin precursor to monatin.

In another embodiment, an enzyme can be added in stage 3 that converts any of the pathway's intermediates into the end product, for example, monatin, or into a pathway that leads to the end product, for example, monatin, but that does not recreate the original pathway. So, for example, an enzyme might be added to convert intermediate Y1 into a downstream intermediate that bypasses the block in the pathway, or that converts the intermediate into the ultimate end product (for example, MP into monatin), but does not allow for the conversion of Y1 into Y2.

One or more cosubstrates or cofactors can be added when the final facilitator, such as the final enzyme, is added, so as to further help drive the final reaction in the direction of the synthesis of the ultimate final product, for example, monatin. Also, one or more than one facilitator, such as one or more than one enzyme can be used to facilitate, that is, catalyze, each reaction in stage 1 and/or stage 3, as desired, including different enzymes of the same class, or different classes of enzymes. Multiple facilitators, for example, multiple enzymes that facilitate the same reaction can be added separately, or, together, for example, as a "blend" (for example, an "enzyme blend"), or set, that contains all or a subset of the desired facilitators or enzymes.

The facilitators, such as the enzymes, that facilitate the reactions in the pathway of the invention can be in solution, together in the reaction mixture. Protein facilitators such as enzymes in solution can be easily removed from the pathway mixture by filtration, especially ultrafiltration, using a membrane that retains substances having molecular weights at least as high as the protein in the reaction mixture that it is desired to separate from the reaction mixture, but that allows the lower molecular weight substances (inter alia, the substrates, the products and intermediates in the pathway) to pass through the membrane.

Protein facilitators, for example, enzymes in solution, can also be easily separated from the lower molecular weight substrates, products and intermediates that are in the reaction mixture by chromatography, for example, column chromatography, for example size exclusion chromatography, ion exchange chromatography or affinity chromatography, where the affinity agent selectively binds one or more of the facilitators, such as an enzyme, as desired, to remove such protein, or all the facilitators from the mixture.

Alternatively, one or more facilitators, such as one or more enzymes, can be bound to solid supports, as desired. Facilitators provided on a solid support can be easily removed from the pathway mixture by, for example, separating the solid supports from the rest of the mixture. See, e.g., Example 10, 13, and 16.

Alternatively, one or more facilitators, such as one or more enzymes can be provided in a contained manner, for example, contained within a semi-permeable membrane that retains the facilitator (for example, retains the enzyme(s)) but allows for the free flow of small molecular weight molecules such as the substrates, intermediates and the ultimate end product and other reaction components. Facilitators, for example, enzymes provided in a contained manner, for example, within a membrane, can be easily removed from the pathway mixture by, for example, removing the membrane from the rest of the mixture.

In one embodiment, only the facilitator, especially, only an enzyme, that catalyzes the intermediate step in the pathway that is to be missing or greatly depressed in stage 3 is provided in stage 1 in such a bound or contained manner.

In another example, the facilitator, especially, an enzyme, that catalyzes the intermediate step in the pathway that is to be missing or depressed in stage three can be provided as a fusion protein in which the fusion partner imparts a property that imparts an ability to remove, inactivate or inhibit the fusion protein in a manner that achieves the result of preventing or greatly depressing conversion of intermediate Yn into the ultimate end product, for example, monatin, in stage 3. For example, the fusion partner may impart the ability to remove the fusion protein by a procedure that depends upon an affinity reaction between the fusion partner and a substance with which it shows affinity.

Further, in the pathway, the one or more reactions that are to be compromised may be compromised by selectively inhibiting the facilitator(s), for example, the enzyme(s) that facilitate such reactions. The inhibition can be reversible or irreversible. Preferably, the inhibitor is a selective inhibitor in the sense that, at the desired reaction conditions, the agent that is responsible for the inhibition inhibits one or more of the facilitators, or enzymes that are present preferentially over other facilitators or enzymes that may also be present. Further, the inhibitor can be one that is capable of being removed from the reaction mixture, for example, or by degradation or inactivation of the inhibitor, for example with a specific wavelength of light, or by physically removing the inhibitor, including for example, removing the inhibitor by dialysis or filtration, including ultrafiltration. For example, class II aldolases can be inhibited by metal chelating agents, for example, EDTA (ethylenediaminetetraacetic acid).

In an example of one embodiment of the invention, one pathway for the synthesis of monatin using biological conversions is exemplified by a pathway that includes, at least, the following three reversible, equilibrium reactions:

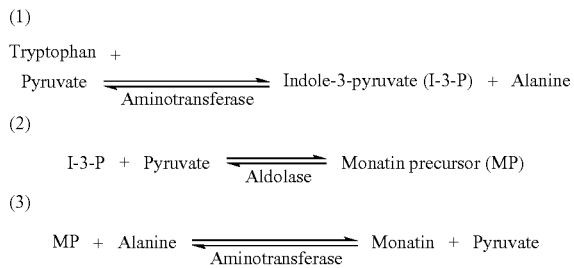

Wherein the tryptophan reaction can optionally include an additional enzyme, a racemase, for example where it is desired to use L-tryptophan as a starting reactant, but ultimately use D-tryptophan (produced from L-tryptophan using a racemase) to produce R,R monatin.

In this pathway, in reaction 1, tryptophan and pyruvate are enzymatically converted to indole-3-pyruvate (I-3-P) and alanine in a reversible reaction. As exemplified above, an enzyme, here an aminotransferase, is used to facilitate (catalyze) this reaction. In reaction (1), tryptophan donates its amino group (to pyruvate) and becomes I-3-P. In reaction (1), the amino group acceptor is pyruvate, which then becomes alanine as a result of the action of the aminotransferase. The preferred amino group acceptor for reaction (1) is pyruvate; the preferred amino group donor for reaction (3) is alanine. The formation of indole-3-pyruvate in reaction (1) can also be performed by an enzyme that utilizes other α-keto acids as amino group acceptors, such as oxaloacetic acid and α-ketoglutaric acid. Similarly, the formation of monatin from MP (reaction 3) can be performed by an enzyme that utilizes amino acids other than alanine as the amino group donor. These include, but are not limited to, aspartic acid, glutamic acid, and tryptophan.

Some of the enzymes useful in connection with reaction (1) are also useful in connection with reaction (3). In the above exemplary reactions, aminotransferase is noted as useful for both of these reactions (1) and (3). The equilibrium constant for reaction (2), the aldolase-mediated reaction of indole-3-pyruvate to form MP is less than one, i.e. the aldolase reaction favors the cleavage reaction generating indole-3-pyruvate and pyruvate rather than the addition reaction that produces the alpha-keto precursor to monatin (i.e. MP). The equilibrium constants of the aminotransferase-mediated reactions of tryptophan to form indole-3-pyruvate (reaction (1)) and of MP to form monatin (reaction (3)) are each thought to be approximately one. Consequently, in order to increase the amount of monatin produced, and enhance the economics of monatin production, it would be desirable to remove one or more products and/or increase the amount of substrates involved in reactions for making monatin. For example, removing the monatin as it is formed will allow the formation of more monatin than if the aldolase and aminotransferase reactions achieve equilibrium; and/or, for example, an increase in the amount of one substrate for reaction (1) or reaction (3) increases the conversion of the second substrate of reaction (1) or reaction (3).

In some embodiments, this invention provides a novel approach that improves the product concentration (or titer) in an equilibrium process, for example up to 1.2 times, 1.3 times, 1.4 times, up to 1.5 times, up to 1.6 times, up to 1.7 times, up to 1.8 times, up to 1.9 times, or up to 2 times the equilibirium amount. In some embodiments, this can be achieved by driving one or more of the reactions in a multi-step pathway in a desired direction. In some instances, the reactions are pushed toward the accumulation of more product, and in others toward the accumulation of more substrates. In accordance with one embodiment of the invention, the reaction materials are brought together to form a first mixture. For reaction (1), above, these reactants include tryptophan (which can be L-tryptophan, D-tryptophan or a combination thereof), pyruvate, an aminotransferase, and optionally a racemase for example when the tryptophan is L-tryptophan but it is desired to use D-tryptophan as listed above for the first reaction, and an aldolase as listed for reaction (2). Alanine (which can be L-alanine, D-alanine or a combination thereof) formed in reaction (1) can react with MP formed in reaction (2) to produce monatin and pyruvate in reaction (3). In the above pathway, reaction 3 can be catalyzed by the same aminotransferase that brings about the first reaction. The mixture can be allowed to reach an equilibrium state at which state an equilibrium amount of monatin will be formed, contained within the first mixture. Removing the monatin from this mixture is possible but it can be more efficient, and result in less of a loss or waste of otherwise useable reactants (including any unstable intermediates), if monatin is simply allowed to remain in the first mixture at this stage. In accordance with this embodiment of the invention, all or at least part of the first mixture is ultrafiltered to create a retentate and a permeate. With proper selection of the molecular weight cutoff for the filter(s) in the ultrafiltration process, the enzymes, an aminotransferase and an aldolase, being of relatively large molecular weight compared to the other constituents of the first mixture, do not pass through the filter, that is, they are are rejected by the filter membrane, and thus remain in, and form, the retentate. The other constituents, for example, tryptophan, pyruvate, alanine, MP and I-3-P, have molecular weights that allow them to pass through the filter and form the permeate.

In an embodiment, an aminotransferase and optionally a racemase (in this case an alanine racemase) is then added to the ultrafiltration permeate along with an increased amount of alanine, creating a second mixture. It may be desirable to use an alanine racemase, for example, where D-tryptophan is a starting material, and excess amounts of D-alanine are desired, which can be obtained by addition of L-alanine and an alanine racemase which facilitates the conversion of L-alanine to D-alanine. Alanine should be added so that it is in excess, or at least not limiting. Preferably alanine is brought to at least a concentration that allows the transaminase to act at or near its maximum velocity, ($V_{max}$), under the desired conditions. The $K_m$ of the enzyme may be used to estimate the concentration of alanine that is needed to ensure the alanine concentration is saturating the enzyme. In the instant embodiment, the enzyme, an aminotransferase, catalyzes reaction (1) and reaction (3). However, the absence of an aldolase or an equivalent facilitator precludes reaction (2) from occurring at an appreciable rate, or at least reduces the rate of the reaction. Additionally, the excess amount of alanine drives reaction (3) in the preferred direction, producing more monatin. And, an increased alanine concentration also pushes reaction (1) in the reverse direction producing tryptophan and pyruvate. This is useful, in part, because I-3-P is a particularly unstable reactant that can decompose into contaminating reaction products. MP is also a relatively unstable constituent in the mixture. The net result is to drive reaction (3) forward toward the production of monatin, to drive reaction (1) backward to the production of initial reactant tryptophan, and to selectively inhibit reaction (2) which otherwise would allow the overall reaction sequence to proceed backward, undesirably converting MP into I-3-P and pyruvate. The monatin can then be removed from the second mixture through a purification process.

In an additional preferred sequence, the retentate, comprising the aminotransferase and aldolase enzymes, can be recycled to the first mixture, or the container where a "new" first mixture is to be reacted or is being reacted. This increases overall process efficiency, utilizing lower quantities of these enzymes for a given monatin output.

In an additional preferred sequence, the purification process to remove monatin from the second mixture utilizes methods developed for the purification of other amino acids. Because monatin is structurally and chemically similar to glutamic acid, methods known in the art for purification of the amino acid glutamic acid from fermentation broths can be used. A description of the isolation of monatin from a complex biological medium is described in WO 2003/091396, Example 6. In that Example, two ion exchange chromatography steps were utilized. First, a strong cation exchange chromatography at a low pH, such as the AG50WX-8 resin (H form) available from Bio-Rad, separated the amino acids from the organic acids. Members of the amino group of the amino acid compounds, such as monatin, are charged and bind to the resin. Any contaminating organic acids are not bound to the resin and flow through the resin at low pH. The amino acids, after elution from the cation exchange resin, may then be separated from each other, such as separating tryptophan, alanine and monatin, using anion exchange chromatography, for example a DEAE resin, at neutral pH. The constituents remaining upon removal of monatin can be recycled back to the first mixture and second mixture. These include, for example, tryptophan, pyruvate, and reduced amounts of MP and I-3-P to the first mixture, and alanine to the second mixture. Reduced amounts refers to the circumstance that reaction (3) has been driven forward, and reaction (1) has been driven backward. Recycling of these reactants further increases overall process efficiency. This is more evident when it is noted that purification or removal of monatin from the reaction mixture typically takes place in acidic conditions. MP and I-3-P decompose in an acidic environment. Thus, in this embodiment, if monatin is removed from the first reaction mixture, without the ultrafiltration and formation of the second mixture, these reactants are at least partially lost, decreasing the monatin production efficiency and creating purification challenges due to the formation of reaction by-products.

These benefits can be realized through the processes of this invention. The production of monatin is increased for a given amount of raw material, the recycle of reactants increases process efficiency, and reactants (e.g., α-carbonyl carboxylates) that otherwise are unstable and can produce undesirable reaction by-products are removed or recycled prior to their detrimental decomposition. However, not all embodiments of the invention need to include all the listed benefits. Some embodiments may include none of the benefits described herein, and some embodiments may include one or more of the benefits described herein.

In accordance with one embodiment of the present invention, a process for producing monatin is provided, which includes producing indole-3-pyruvate from tryptophan, producing 2-hydroxy 2-(indol-3ylmethyl)-4-ketoglutaric acid ("monatin precursor" or "MP") from indole-3-pyruvate, and producing monatin from MP. For example, if L-tryptophan (also called S-tryptophan) is the substrate, the reaction to produce indole-3-pyruvate can be facilitated by an enzyme having substrate selectivity for S-amino acids. If 2S isomers of monatin are desired, the reaction of indole-3-pyruvate with pyruvate to form the S-isomer of MP can be facilitated by an enzyme having S-selective aldolase activity. Similarly, if the 4S isomers of monatin are desired, the reaction of MP to produce monatin can be facilitated by an enzyme having selectivity for L-amino acid substrates. Similarly, other isomeric products can be distinctively produced using enzymes with different substrate selectivities. For example, in some cases the 2R or the 4R isomer of monatin is the preferred product and the use of an enzyme with a substrate stereoselectivity for R-substrates can facilitate the formation of the preferred product. The term "stereoselective" means that an enzyme has greater specificity, greater activity, or both for one stereoisomer. A stereoselective enzyme having limited activity for one stereoisomer as compared to another can be used. "Limited" activity means activity that is minimal or not perceptible, for example as determined according to experiments.

Where references are made to a series of reactions such as in the preceding paragraphs, the invention does not require each step to be explicitly performed; it is sufficient that the steps may be implicitly performed. In other words, for example, the process for producing monatin, which includes producing indole-3-pyruvate from tryptophan, producing 2-hydroxy 2-(indol-3ylmethyl)-4-ketoglutaric acid ("monatin precursor" or "MP") from indole-3-pyruvate, and producing monatin from MP, wherein each reaction is facilitated by an appropriate enzyme, can be performed by combining tryptophan with the enzymes and setting conditions so that the enumerated reactions could occur. In such an instance, tryptophan could react to produce indole-3-pyruvate, the indole-3-pyruvate produced from the tryptophan reaction could react to form MP, and the MP produced from the indole-3-pyruvate reaction could react to form monatin. The process could also be performed, by way of example, by providing a compound that can produce tryptophan, under conditions suitable for tryptophan production to occur and combining that compound with enzymes capable of facilitating the series of reactions set forth under conditions which would be suitable for those reactions to occur. For example, a microorganism which naturally produces large amounts of L-tryptophan (or D-tryptophan) could be provided as a source of the tryptophan. For example, D-tryptophan can be provided by providing L-tryptophan and an enzyme with broad specificity amino acid racemase activity or tryptophan racemase activity and conditions which would be suitable for the conversion of L to D tryptophan to occur.

In certain embodiments, particular permutations can be designed to make the production of monatin (e.g., R,R monatin) more economical. For example, L-tryptophan, as opposed to D-tryptophan or combinations of L- and D-tryptophan, can act as the starting material. While the choice of the specific form of tryptophan does not impact the chirality of the ultimate monatin compounds in the monatin composition (because the tryptophan reaction forms indole-3-pyruvate, which has no chirality), some may prefer utilizing L-tryptophan as a starting material at least because L-tryptophan is currently less expensive and more easily obtainable than D-tryptophan.

In another embodiment, the invention provides a process for producing monatin that includes producing D-tryptophan from L-tryptophan, producing indole-3-pyruvate from D-tryptophan, producing R-MP from indole-3-pyruvate, and producing R,R-monatin from R-MP. The production of D-tryptophan from L-tryptophan can be facilitated by a tryptophan racemase and functional equivalents thereof. Similarly, the reactions of D-tryptophan to form indole-3-pyruvate and of MP to form monatin can be facilitated by the same enzyme. The reaction of indole-3-pyruvate can be facilitated by an enzyme having R-specific aldolase activity; and consequently R-MP is formed. The reactions of D-tryptophan to form indole-3-pyruvate and of R-MP to form R,R-monatin can be facilitated by the same enzyme.

In some embodiments, in accordance with the present invention, a process for producing monatin is provided, which includes producing indole-3-pyruvate from L-tryptophan, producing 2-hydroxy 2-(indol-3ylmethyl)-4-keto glutaric acid ("monatin precursor" or "MP") from indole-3-pyruvate, and producing monatin from MP. The reaction of L-tryptophan to produce indole-3-pyruvate is facilitated by an enzyme having greater specificity, greater activity, or both for L-tryptophan as a substrate than for R-MP, R,R monatin, or both. Examples of enzymes having greater activity and/or greater specificity for L-tryptophan as a substrate than for either MP or monatin include, but is not limited to L-tryptophan aminotransferases, L-aromatic aminotransferases, L-aspartate aminotransferases, and L-amino acid oxidases. According to certain embodiments, the reaction of indole-3-pyruvate is facilitated by an enzyme having R-specific aldolase activity and consequently produces R-MP. According to some embodiments, an aminotransferase specific for D-amino acids (called a D-aminotransferase) also has greater specificity, greater activity, or both for the R-MP as a substrate than for indole-3-pyruvate. In certain other embodiments, the D-aminotransferase has limited activity for the indole-3-pyruvate as a substrate.

According to certain embodiments, a racemase enzyme is provided that can facilitate epimerization of the amino acid that is formed as a byproduct of the L-tryptophan transamination reaction (or that is formed from another amino acid that is a byproduct of the tryptophan reaction) from one isomeric form to another isomeric form.

Non-limiting examples of such enzymes include glutamate racemases (EC 5.1.1.3) or functional equivalents that can facilitate the conversion of L-glutamate to D-glutamate, aspartate racemases (EC 5.1.1.13) or functional equivalents that convert L-aspartate to D-aspartate, alanine racemases or functional equivalents that convert L-alanine to D-alanine (EC 5.1.1.1).

In other embodiments according to the invention, a process for producing monatin is provided, in which an α-keto acid substrate forms an L-amino acid when L-tryptophan is converted to indole-3-pyruvate, indole-3-pyruvate reacts to form MP (which can include both R-MP and S-MP though preferably includes only or predominately R-MP), and the L-amino acid reacts to regenerate (also referred to as "recycle") the α-keto acid substrate when R-MP is converted to R,R monatin. The reaction of R-MP and an L-amino acid to form R,R monatin is facilitated by a stereoinverting aminotransferase. In this way, the L-amino acid product of the L-tryptophan aminotransferase reaction may be used as a substrate for the transamination of MP to monatin, and the product (i.e. oxaloacetate, pyruvate, and/or α-KG) of the reaction coupled to the MP to monatin reaction can be used as a starting material for the reaction coupled to the L-tryptophan to indole-3-pyruvate reaction. Non-limiting examples of stereoinverting aminotransferases that may be used include mutants derived from D-phenylglycine aminotransferase (EC 2.6.1.72, also known as D-4-hydroxyphenylglycine aminotransferase), D-methionine aminotransferase (EC 2.6.1.41, also known as D-met-aminotransferase and D-methionine-pyruvate aminotransferase), and homologs thereof.

Further embodiments can be found in U.S. application Ser. No. 11/714,279 filed Mar. 6, 2007 (see, e.g., FIGS. 1 and 3), which is herein incorporated by reference in its entirety. In certain embodiments, the overall pathway to produce monatin can involve a reaction of tryptophan to form indole-3-pyruvate, a reaction of indole-3-pyruvate to produce MP, and a reaction of MP to produce monatin, including R,R monatin. Although, as would be evident to one of ordinary skill in the art, various permutations to this pathway can be made without deviating from the overall scope of the disclosure.

In one such embodiment, a permutation may be made to the pathway to increase the production of the R,R form of monatin at the expense of the S,S, R,S, and S,R forms of monatin. In particular, the aminotransferase enzyme utilized in the L-tryptophan reaction has greater activity and/or specificity for that reaction versus the reactions of MP and 4S monatin or the oxidase has greater activity and/or specificity for L-tryptophan than for 4R monatin; the enzyme which facilitates the reaction of indole-3-pyruvate is an R-specific aldolase; and the enzyme which facilitates the reaction of MP is a broad specificity D-enzyme, preferably evolved to work more efficiently with the R isomer of MP. In certain cases, the indole-3-pyruvate can then be produced indirectly, rather than directly from L-tryptophan. More specifically, L-tryptophan is converted to D-tryptophan, and D-tryptophan is then converted to indole-3-pyruvate.

In a specific embodiment, L-tryptophan is converted to D-tryptophan using a tryptophan racemase. D-tryptophan then reacts with pyruvate via a broad specificity D-aminotransferase to produce indole-3-pyruvate and D-alanine. Indole-3-pyruvate then reacts with an R-specific aldolase and pyruvate to form R-α-keto acid monatin (R-MP). R-MP then reacts with a broad specificity D-aminotransferase and D-alanine to produce R,R monatin and pyruvate.

The conversion of L-tryptophan to D-tryptophan can be facilitated by a tryptophan racemase or functional equivalent thereof. Exemplary types of enzymes with tryptophan racemase activity include Broad Activity Racemases from *Pseudomonas* and *Aeromonas* species (Kino, K. et al., Applied Microbiology and Biotechnology (2007), 73(6), 1299-1305; Inagaki, K. et al, Agricultural and Biological Chemistry (1987), 51(1), 173-80).

For additional examples of racemases, aldolases, and aminotransferases, see, for example, U.S. application Ser. No. 11/714,279 filed Mar. 6, 2007.

The pathway discussed above can have certain benefits, including that even when R,R monatin is the desired product, the same enzyme can be used for the reaction that produces indole-3-pyruvate as for the reaction that produces monatin as a product. For example, in some cases an L-aminotransferase (or suitable L-enzyme) can facilitate the reaction producing indole-3-pyruvate, but a D-aminotransferase facilitates the reaction producing monatin. By contrast, a certain D-aminotransferase that facilitates the reaction producing indole-3-pyruvate, can also facilitate the reaction producing monatin. Consequently, broad specificity D-aminotransferases may be preferred when there is a desire to use the same enzyme for the reaction forming indole-3-pyruvate as for the reaction forming monatin. In certain cases, production of monatin may be more efficient when a D-aminotransferase is chosen that has limited activity and/or specificity for indole-3-pyruvate as compared to R-MP.

An additional benefit of the above pathway is that the amino acid product of the reaction coupled to the reaction producing indole-3-pyruvate can be used as a substrate in the reaction coupled to the reaction producing monatin. For example, if L-tryptophan reacts to produce indole-3-pyruvate and at the same time oxaloacetate, α-ketoglutarate, and/or pyruvate react to produce an L-amino acid, and the reaction of R-MP to form monatin is coupled with a reaction utilizing a D-amino acid as a substrate, then the L-amino acid of the reaction forming indole-3-pyruvate is not, under the conditions described, recycled for use in the reaction coupled to the R-MP reaction. By contrast, if the reaction of D-tryptophan to form indole-3-pyruvate is coupled to a reaction forming a D-amino acid product, then the D-amino acid can be recycled for use in the reaction coupled to the R-MP reaction. This allows one to use non-stoichiometric amounts of amino acceptor in the first step, and the amino donor needed for the third step is produced in the first. In specific embodiments, the D-amino acid is D-alanine.

A person having ordinary skill in the art would understand from the present disclosure how to implement the present invention to improve the yield of R,R monatin in the various pathways. For example, a person of ordinary skill would understand from the disclosure that an embodiment of the invention, as applied to production of R,R monatin, includes providing a first mixture of reactants and facilitators under appropriate conditions to allow the first mixture to produce R,R monatin; removing at least the enzymes(s) that facilitate reactions which compete with the step in the pathway that directly produces monatin (generally the last step in the pathway), or at least removing the enzymes in a manner that disrupts reactions resulting in reducing the concentration of unstable intermediates, or removing all of the enzymes, after the first reaction has proceeded for a desired time, for example until equilibrium is reached; followed by the addition of at least one enzyme which functions in monatin-producing step of the pathway (generally the final step of the pathway), and optionally adding other components whose increased concentration assists the equilibrium of the monatin-producing step to move toward production of monatin, thereby increasing the production or R,R monatin. See, e.g., Example 9 and 14.

In one such embodiment, L-tryptophan is converted to D-tryptophan using a tryptophan racemase. D-tryptophan then reacts with pyruvate via a broad specificity D-aminotransferase to produce indole-3-pyruvate and D-alanine. Indole-3-pyruvate then reacts with an R-specific aldolase and pyruvate to form R-α-keto acid monatin (R-MP). R-MP then reacts with a broad specificity D-aminotransferase and D-alanine to produce R,R monatin and pyruvate. To increase the production of R,R monatin, one or more of the enzymes is removed from the reaction (e.g., an R-specific aldolase) to inhibit or slow those reaction which are competitive with production of R,R monatin. In certain embodiments, the remaining reaction mixture is supplemented with the enzyme responsible for production of monatin (e.g., D-aminotransferase), and in specific cases, an amino donor (e.g., D-alanine) is also added.

Figure 2:
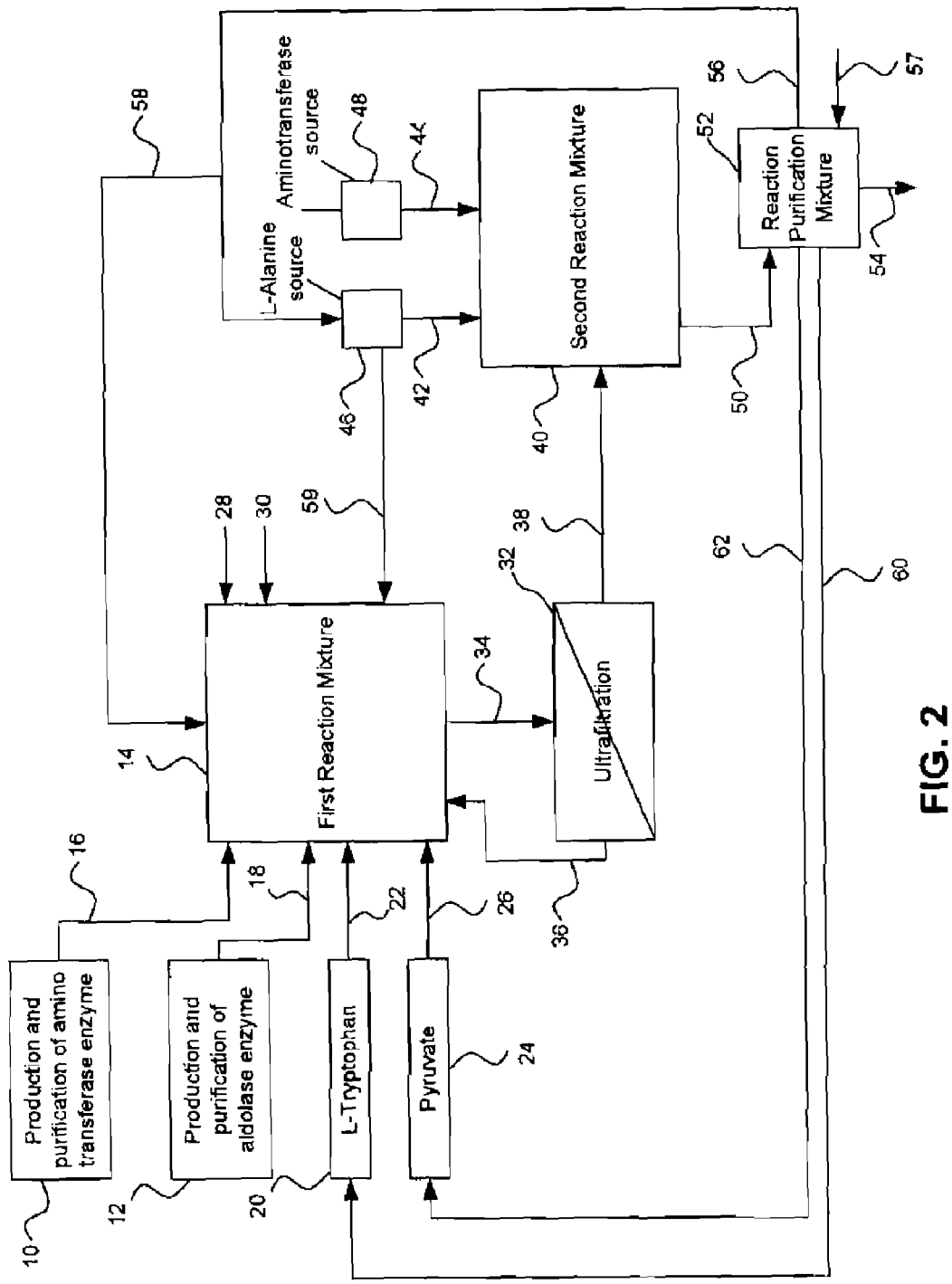
FIG. 2 is a schematic block diagram of a system that exemplifies production of monatin in accordance with an embodiment of this invention.

A process flow chart, in accordance with the invention is shown in FIG. 1 and a block diagram of an exemplary system in accordance with the invention is shown in FIG. 2. FIG. 2 identifies pathways for producing monatin, but is not intended to be limited to any particular method or system for practicing the pathways. For example, when practiced in vitro, none of the reactions in the pathway are performed inside a living whole cell. Alternatively, the methods may be practiced utilizing a combination of in vitro and in vivo methods. For example, the amino acid produced in reaction (1) by the deamination of tryptophan can be utilized in reaction (3) to produce monatin from MP, and thus does not have to be explicitly provided by the practitioner. Furthermore, practice does not require that each of the identified components (e.g., reactants and enzymes) is explicitly provided by the practitioner, so long as sufficient components, or sources of components, and reaction conditions are provided or present so that the pathway can potentially proceed. For example, it is contemplated that practice of a pathway that uses L-tryptophan as a starting material would include not only embodiments in which L-tryptophan is provided, but also embodiments in which a compound is provided that can produce L-tryptophan, under conditions suitable for L-tryptophan production to occur from that compound, and combining that compound with enzymes capable of facilitating the reaction or the series of reactions for such conversion of that compound to L-tryptophan. Thus, for example, for the embodiment exemplified by reactions (1), (2) and (3), above, the reaction mixture need not exclusively contain only the reactants and products of the three reactions. Secondary reactions and/or by-products, such as an aldolase catalyzed addition of one pyruvate molecule with a second pyruvate molecule, may also be present (4-hydroxy-4-methyl-2-oxoglutarate, or "HMO"). The HMO may also undergo a transamination reaction to produce 4-hydroxy-4-methyl glutamate ("HMG"). The HMG may be recycled into reaction mixture one to prevent further loss of pyruvate and amino groups that would otherwise be available for the reactions to produce monatin.

Referring now to FIG. 1, as indicated in block 1, at least one reactant and at least one enzyme are added to a first reaction vessel. FIG. 2 will be referred to as an exemplary system for carrying out the process outlined in FIG. 1. As exemplarily shown in FIG. 2, an aminotransferase enzyme is produced and purified, or otherwise provided in a subsystem 10, and aldolase enzyme is produced and purified, or otherwise provided, in a subsystem 12. These catalysts are conveyable to a first reaction vessel 14 through conduits 16, 18. In an alternate embodiment the necessary enzymes can be introduced from a single source and fed to the first reaction vessel through a single conduit. Origination material L-tryptophan (or alternatively D-tryptophan or a mixture of L- and D-tryptophan) is conveyable from a tryptophan source 20 through conduit 22 to first reaction vessel 14 and origination material pyruvate is conveyable from a pyruvate source 24 through conduit 26 to first reaction vessel 14. If desired, original material L-alanine (or alternatively D-alanine or a mixture of L- and D-alanine) is conveyable from an L-alanine source 46 through conduit 59 to first reaction vessel 14. Other conduits 28, 30 are available for conveyance of additional reactants or compositions to the first reaction vessel 14. As indicated in block 2 of FIG. 1, the at least one reactant and at least one enzyme react to form a first reaction mixture.

As indicated in block 3 of FIG. 1, at least one enzyme present in the first reaction mixture is inactivated after a predetermined time. The inactivation of the enzyme(s) can include inhibiting the enzyme(s) or removing/separating the enzyme(s) from the first reaction mixture. FIG. 2. illustrates an exemplary system wherein the enzyme(s) is separated from the first reaction mixture through ultrafiltration. While ultrafiltration is utilized in this embodiment, other separation systems and processes known to those skilled in the art can be utilized for removing/separating enzyme(s) from the first reaction mixture, for example immobilized enzymes. The first reaction vessel 14 is connected to an ultrafiltration system 32 through a conduit 34. The first reaction mixture, containing the constituents of the equilibrium reactions (1), (2) and (3) is conveyable through conduit 34 into the ultrafiltration system 32, at a desired time. The ultrafiltration system separates the first reaction mixture into a retentate comprising the larger molecular weight enzymes aminotransferase and aldolase, and a permeate comprising the other constituents in the first reaction mixture. The enzymes are recyclable, directly or indirectly, to the first reaction vessel through conduit 36. The enzymes can, for example, be separated from one another and recycled or otherwise used separately in appropriate quantities. The permeate is conveyable through conduit 38 to a second reaction vessel 40.

As indicated in block 4, after the inactivation of the at least one enzyme the inactivated mixture is fed to a second reaction vessel. An additional enzyme(s) is also added to the second reaction vessel and the constituents react to form a second reaction mixture, as indicated in blocks 5 and 6, respectively. As exemplary shown in FIG. 2, the constituents conveyed as the permeate into the second reaction vessel 40 include tryptophan, pyruvate, alanine, MP, I-3-P and monatin. Inlet conduits 42, 44 convey additional reagents or reagent quantities into the second reaction vessel 40. These additional reagents can include, for example, alanine from an alanine source 46 connected to inlet conduit 42, and aminotransferase or other enzymes from an aminotransferase source 48 connected to inlet conduit 44. The reactants that exist in the second reaction vessel 40 form a second reaction mixture and are those that engage in equilibrium reactions (1) and (3), but not equilibrium reaction (2) because of the absence of aldolase enzyme. The second reaction mixture is enriched in monatin compared to the monatin concentration in the first reaction mixture.

The second reaction mixture is subsequently purified to remove monatin, the desired product, as indicated in block 7. As exemplarily shown in FIG. 2, the second reaction mixture is conveyable through a conduit 50 into a monatin purification subsystem 52. Other constituents are added in the purification system through, for example, a conduit 57 to form a reaction purification mixture in the purification system. Monatin purification subsystems are well known, and typically operate in an acidic environment. One typical system comprises cation exchange chromatography. Monatin is removable from the purification system 52 through conduit 54. Among the other constituents, alanine is removable through a conduit 56. Conduit 56 can be used to recycle alanine to the alanine source 46 and second reaction vessel 40, (or through a conduit 58 to first reaction vessel 14). Other constituents, such as tryptophan and pyruvate, can be recycled to the first reaction vessel 14. Tryptophan is conveyable through conduit 60 to tryptophan source 20, and pyruvate is conveyable through conduit 62 to pyruvate source 24.

Figure 3:
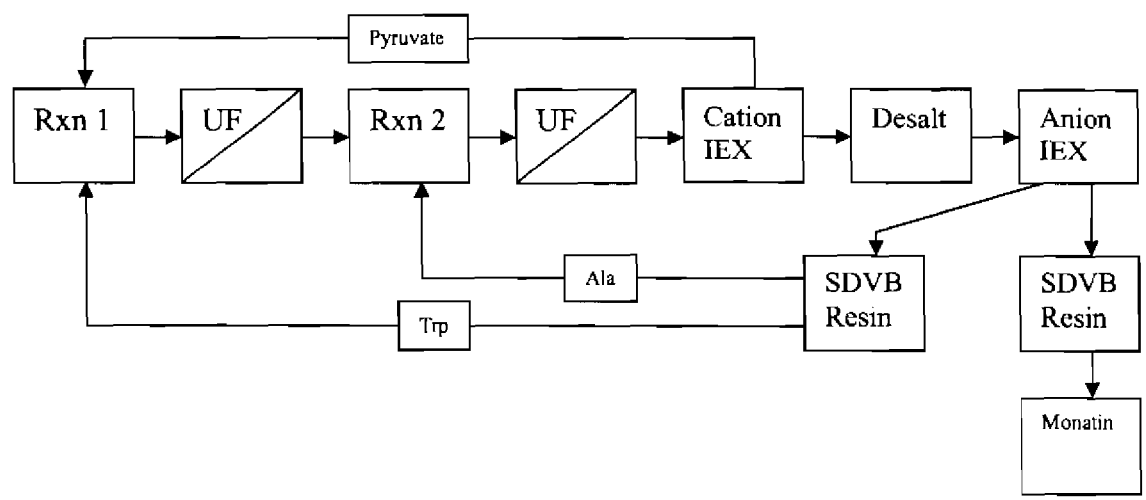
FIG. 3 is a schematic block diagram of a system that exemplifies the separation of various components in the production of monatin in accordance with various embodiments of the invention.

Examples of various purification methods as shown in the reaction purification mixture 52 of FIG. 2 can be found in FIGS. 3-7. The Figures refer to various procedures such as ultrafiltration, cation exchange chromatography, anion exchange chromatography, non-polar synthetic adsorbent chromatography, and desalting. In some ultrafiltration embodiments, the membrane may have an effective cutoff of about 10 kda, 20 kda, 30 kda, or 50 kda. In some embodiments, the membrane material may be from regenerated cellulose, polysulfone ether, ceramic, stainless steel, or any other suitable material. In some cation exchange chromatography embodiments, the cation exchange column is a stong acid cation exchange resin in H+ form, having a styrene divinylbenzene copolymer functionalized with sulfonic acid and including a crosslinking of from about 2-12%. In some embodiments, elution is with caustic solution such as solutions of KOH, NaOH, NH$^4$OH, or combinations thereof, which are then neutralized with an acid such as HCl, carbonic, sulfuric, nitric, formic, citric or acetic acid. In some anion exchange chromatography embodiments, the anion exchange chromatography column is a strong anion exchange resin of, for example, polymethacrylate polymer for minimizing non-specific binding in hydroxide, acetate, or carbonate form. In some embodiments, elution is with potassium hydroxide, ammonium bicarbonate, potassium acetate, sodium acetate, sodium hydroxide, sodium bicarbonate, potassium bicarbonate, ammonium acetate, ammonium hydroxide, or combinations thereof, which are then neutralized with, for example, HCl, carbonic, sulfuric, nitric, formic, citric or acetic acid. In some embodiments, the non-polar synthetic adsorbent resin is a styrene divinylbenzene copolymer having: a specific surface area of at least 600 m$^2$/g, or even 1000 m$^2$/g, or higher; a pore radius of about 150 angstroms or less. In some embodiments, the column is washed with water or aqueous ethanol of 15% v/v concentration or less. In some embodiments, desalting can include evaporation if the salts are volatile as with ammonium bicarbonate, or may be done by passing through a synthetic non-polar adsorbent column. Referring to FIG. 3, reaction mixture 2 is passed through an ultrafiltration system (see, e.g., Example 17), yielding a retentate including the enzymes and a permeate including the substrates, intermediates, and products and other small molecules of the first reaction mixture. The permeate of ultrafiltration is then passed through a cation exchange column. Pyruvate is separated and recycled into the first reaction mixture. Following cation exchange, the mixture is desalted and run through an anion exchange column (see, e.g., Example 18). The anion exchange column is able to separate the desired product, monatin, from the reactants tryptophan and alanine. The product, monatin, is further purified using an SDVB resin (see, e.g., Example 20). The reactants tryptophan and alanine are also purified by way of an SDVB resin, and are then recycled into reaction mixture 1 or 2, respectively.

Figure 4:
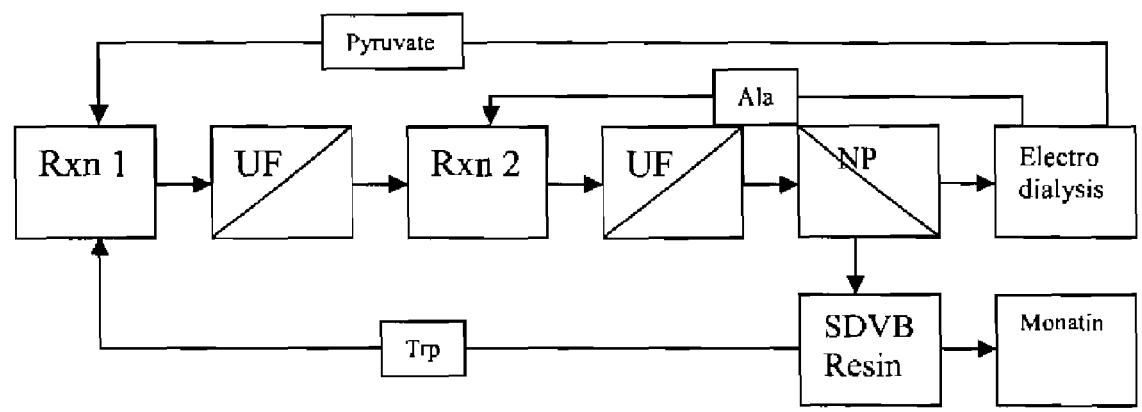
FIG. 4 is a schematic block diagram of a system that exemplifies the separation of various components in the production of monatin in accordance with various embodiments of the invention.

Referring to FIG. 4, the reaction purification mixture can be purified in a modification of that shown in FIG. 3. As in FIG. 3, reaction mixture 2 is initially purified by ultrafiltration, but in this case, the permeate is first purified using a specialty membrane purification step (NP) (see, e.g., Example 19), wherein the membrane is designed to separate small from large compounds. The NP can separate tryptophan and the desired product, monatin, from the reaction mixture. The monatin and tryptophan are separated from one another by way of an SDVB resin. The remaining components of the NP separation are further purified by electrodialysis (see, e.g., Example 21). This process purifies and separates pyruvate and alanine for recycling and further use in reaction mixture 1 and 2, respectively.

Figure 5:
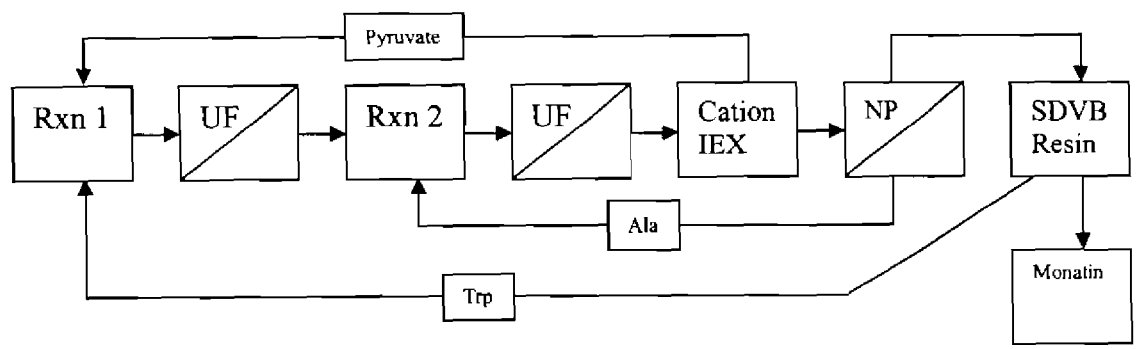
FIG. 5 is a schematic block diagram of a system that exemplifies the separation of various components in the production of monatin in accordance with various embodiments of the invention.

FIG. 5 illustrates another method of purification. As with the above examples, the first step in the purification of reaction mixture 2 is ultrafiltration. Following ultrafiltration, pyruvate is removed from the permeate via cation exchange chromatography, which can separate amino acids from organic acids. This reactant can then be recycled back into reaction mixture 1. The remaining reaction mix after cation exchange is processed through an NP membrane to separate alanine from the reaction mixture. As described above, the alanine can then be recycled into reaction mixture 2. The remaining reaction mixture is processed through an SDVB resin to separate and purify tryptophan, and the desired product, monatin.

Figure 6:
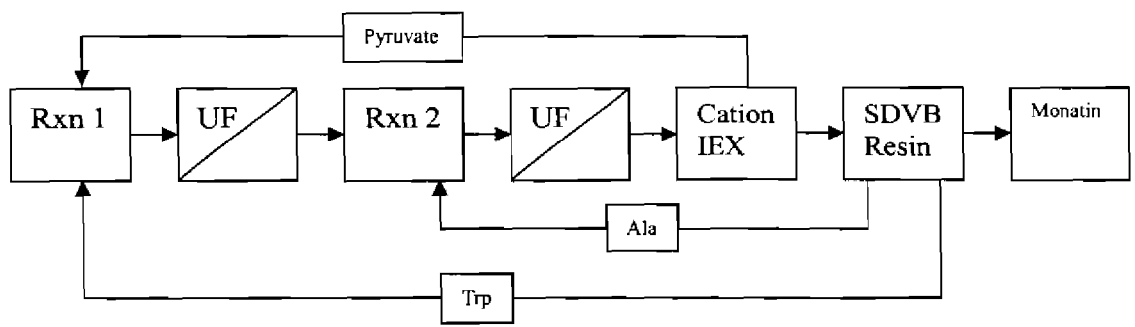
FIG. 6 is a schematic block diagram of a system that exemplifies the separation of various components in the production of monatin in accordance with various embodiments of the invention.

Another example of the purification of reaction mixture 2 can be found in FIG. 6. Following the initial ultrafiltration of reaction mixture 2, pyruvate is once again removed using cation exchange chromatography for recycling into reaction mixture 1. After cation exchange, the remaining reaction mixture is processed through an SDVB resin to separate and purify alanine and tryptophan for recycling, as well as the desired product, monatin. Depending on the load capacity of the resin, a person of ordinary skill would understand that the process (as exemplified in this figure or in others) may require more than one SDVB resin and/or more than one SDVB resin processing step. An example of the separation of alanine from monatin is shown in Example 20.

Figure 7:
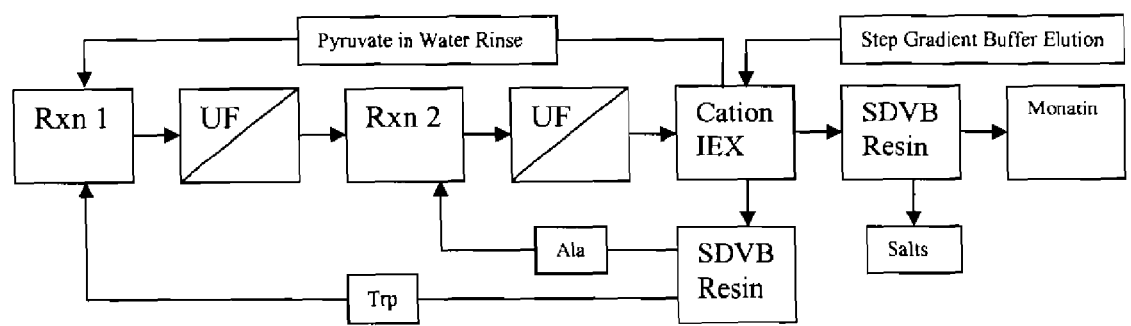
FIG. 7 is a schematic block diagram of a system that exemplifies the separation of various components in the production of monatin in accordance with various embodiments of the invention.

In a further example, FIG. 7 details another permutation of the purification of reaction mixture 2. Following ultrafiltration, cation exchange is used in conjunction with a step gradient buffer elution to separate three fractions (see, e.g., Example 22). In one of the fractions, pyruvate is removed in the water rinse. In another of the fractions, alanine and tryptophan are removed and further processed by an SDVB resin prior to recycling them into reaction mixtures 1 and 2 as described above. The final fraction is also further processed via an SDVB resin to separate out both the salts of the reaction mixture and the desired product, monatin.

Another example of the purification of reaction mixture 2 is to utilize anion exchange chromatography followed by a desalting column. Following the initial ultrafiltration of reaction mxture 2, anion exchange chromatography is performed under conditions in which alanine and tryptophan do not bind, and can be recycled to reaction mix 1. The organic acids and monatin of the original reaction mixture 1 bind and can be selectively eluted using a gradient. Monatin can be desalted using the SDVB resin as described above.

The block diagram as shown in FIG. 2 can be modified as necessary to replace the enzymes and substrates with any enzyme or combination of enzymes, or substrate or combination of substrates, useful for the alternate embodiments of the invention. For example, the exemplified transferase enzyme provided by subsystem 10 and the exemplified aldolase enzyme provided by subsystem 12, can be replaced with any enzyme or combination useful for facilitating one or more reactions in the synthetic pathway. In a similar manner, L-tryptophan source 20 and pyruvate source 24 would instead provide the appropriate substrates for the enzymes provided in subsystems 10 and/or 12. For example, "L-tryptophan" could be "D-tryptophan" or a D-tryptophan source, or a mixture of L- and D-tryptophan. As another example, "L-alanine" could be "D-alanine" or a mixture of L- and D-alanine, or another amino acid, as appropriate for the various monatin-producing pathways.

Exemplary enzymes useful in the methods of the invention for converting tryptophan to indole-3-pyruvate (reaction 1) include members of the enzyme classes (EC) 2.6.1.27, 1.4.1.19, 1.4.99.1, 2.6.1.28, 1.4.3.2, 1.4.3.3, 2.6.1.5, 2.6.1.-, 2.6.1.1, 2.6.1.21 and 3.5.1.-. These classes include polypeptides such as: tryptophan aminotransferase (see, e.g., Example 7), which converts L-tryptophan and α-KG (i.e., α-ketoglutarate, also called 2-oxoglutarate) to indole-3-pyruvate and an amino acid such as L-glutamate; D-tryptophan aminotransferase, which converts D-tryptophan and a 2-oxo acid to indole-3-pyruvate and an amino acid; tryptophan dehydrogenase, which converts L-tryptophan and NAD(P) to indole-3-pyruvate and NH$_3$ and NAD(P)H; D-amino acid dehydrogenase, which converts D-amino acids and FAD to indole-3-pyruvate and $NH_3$ and $FADH_2$; tryptophan-phenylpyruvate transaminase, which converts L-tryptophan and phenylpyruvate to indole-3-pyruvate and L-phenylalanine; L-amino acid oxidase, which converts an L-amino acid and $H_2O$ and $O_2$ to a 2-oxo acid and $NH_3$ and $H_2O_2$; D-amino acid oxidase, which converts a D-amino acid and $H_2O$ and $O_2$ to a 2-oxo acid and $NH_3$ and $H_2O_2$; and tryptophan oxidase, which converts L-tryptophan and $H_2O$ and $O_2$ to indole-3-pyruvate and $NH_3$ and $H_2O_2$. These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid. In addition, these classes include phenylalanine deaminases, which can convert tryptophan to indole-3-pyruvate and ammonium in the presence of water.

Exemplary enzymes useful in the methods of the invention for the conversion of indole-3-pyruvate to MP (reaction 2) include members of the enzyme classes 4.1.3.-, 4.1.3.16, 4.1.3.17, and 4.1.2.-. These classes include carbon-carbon synthases/lyases, such as aldolases (see, e.g., Example 8, 11, and 12) that catalyze the condensation of two carboxylic acid substrates. Peptide class EC 4.1.3.- are synthases/lyases that form carbon-carbon bonds utilizing oxo-acid substrates (such as indole-3-pyruvate) as the electrophile, while EC 4.1.2.- are synthases/lyases that form carbon-carbon bonds utilizing aldehyde substrates (such as benzaldehyde) as the electrophile. For example, KHG [2-keto-4-hydroxyglutarate]aldolase (EC 4.1.3.16) and ProA aldolase (EC 4.1.3.17), are known to convert indole-3-pyruvate and pyruvate to MP. Although ProA aldolase can be thought to identify only the 4-hydroxy-4-methyl-2-oxoglutarate (HMG) aldolase derived from Comamonas testosteroni, herein the term ProA aldolase is used to mean any polypeptide with 4-hydroxy-4-methyl-2-oxoglutarate aldolase activity unless otherwise stated. Suitable examples of Pro aldolases include Comamonas testosteroni ProA (correlating to SEQ ID NO 65 (nucleic acid sequence) in U.S. Patent Publication No. 2005/0282260, herein incorporated by reference, and SEQ ID NO:66 (amino acid sequence) also in U.S. Patent Publication No. 2005/0282 and Sinorhizobium meliloti (HMG Aldolase) ProA (NCBI Accession No.: CAC46344), or enzymes that display homology to Comamonas testosteroni ProA (SEQ ID NO 65 (nucleic acid sequence) in U.S. Patent Publication No. 2005/ 0282260, SEQ ID NO: 66 (amino acid sequence) in U.S. Patent Publication No. 2005/0282260) and/or Sinorhizobium meliloti (HMG Aldolase) ProA (NCBI Accession No.: CAC46344), and/or the aldolase encoded by SEQ ID NO: 1 (nucleic acid sequence) or SEQ ID NO:2 (amino acid sequence), and/or the aldolase described in Example 8. For example, suitable enzymes may have at least about 40%, 50%, 60%, 70%, 80%, 90%, 95%, and/or 99% amino acid sequence identity with Comamonas testosteroni ProA (SEQ ID NO:66 of U.S. Patent Publication No. 2005/0282260) and/or Sinorhizobium meliloti ProA (NCBI Accession No.: CAC46344) and/or SEQ ID NO:2 and/or the aldolase described in Example 8. MP can also be generated using chemical reactions, such as the aldol condensations.

Exemplary enzymes useful in the methods of the invention for the conversion of MP to monatin (reaction 3) include members of the enzyme classes: tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (EC 1.4.1.20), tryptophan-phenylpyruvate transaminases (2.6.1.28), or more generally members of the aminotransferase family (2.6.1.-) such as aspartate aminotransferase (EC 2.6.1.1), tyrosine (aromatic) aminotransferase (2.6.1.5), D-tryptophan aminotransferase, or D-alanine (also known as D-aspartate or D-amino acid) (2.6.1.21) aminotransferase (see FIG. 2 of WO 03/091396 A2). This reaction can also be performed using chemical reactions. Amination of the keto acid (MP) is performed by reductive amination using ammonia and sodium cyanoborohydride. FIGS. 11-13 of WO 2003/091396 A2 show additional polypeptides that can be used to convert MP to monatin, as well as providing increased yields of monatin from indole-3-pyruvate or tryptophan.

Provided herein is a method for increasing the overall yields of a product or products in a multi-step equilibrium reaction beyond the yield which is obtained by the equilibrium process alone. In certain embodiments such a method can include allowing the components of an equilibrium reaction (e.g., reactants and facilitators) to proceed for some period of time (e.g., to reach equilibrium). After this period of time, the reaction can be altered through the removal of one or more facilitators (e.g., enzymes). Such facilitators can include those which facilitate reactions that are competitive with the production of product. For example, such competitive reactions can include any reverse reactions within the equilibrium process. In certain cases only the competitive reactions will be altered, while in others all of the reactions will be altered or broken. Once the these reactions have been altered or broken, the reaction directly producing product is restarted through the addition of the facilitator(s) responsible for production of the product(s), for example, generally the facilitators involved in the last step of the multi-step pathway are reintroduced to the mixture to restart the final step of the pathway.

A person having ordinary skill in the art, in reading the present disclosure, would understand that the methods described herein could be adapted to produce derivatives of monatin, as analogous pathways and enzymes can be used in the production of the monatin derivatives. For example, such a derivative could include that discussed in U.S. application Ser. No. 11/58,4016, filed Oct. 20, 2006, which is herein incorporated by reference in its entirety. This derivative could have the following structure:

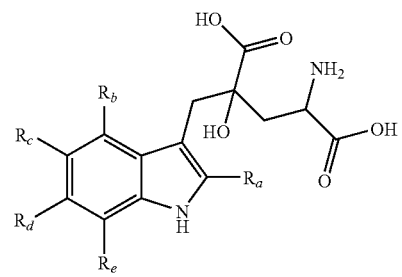

wherein $R_a$, $R_b$, $R_c$, $R_d$, and $R_e$ each independently represent any substituent selected from a hydrogen atom, a hydroxyl group, a $C_1$-$C_3$ alkyl group, a $C_1$-$C_3$ alkoxy group, an amino group, or a halogen atom, such as an iodine atom, bromine atom, chlorine atom, or fluorine atom. However, $R_a$, $R_b$, $R_c$, $R_d$, and $R_e$ cannot simultaneously all be hydrogen. Alternatively, $R_b$ and $R_c$, and/or $R_d$ and $R_e$ may together form a $C_1$-$C_4$ alkylene group, respectively.

The systems described herein for the methods of the invention can be automated, or semi-automated. Further, the invention provides for an apparatus that utilizes the methods or systems of producing monatin as described herein, and methods for using such apparatus. Such an apparatus comprises: a first reaction vessel, a separation vessel and a second reaction vessel. The first reaction vessel may have one or more feeds or conduits that can provide the constituents (one or more enzymes and/or one or more substrates or other components) of a mixture that is to be present in the first reaction vessel. The separation vessel contains the first reaction mixture in a manner that retains a desired enzyme, protein or facilitator while permitting transfer of desired components from the first reaction vessel into a second reaction vessel. The second reaction vessel may also have one or more feeds or conduits for protein/enzyme or component additions, and may further have one or more outlets to facilitate recycling of certain components of the second reaction mixture back into the first reaction vessel, and to facilitate collection of the desired end product.

The separation vessel may be part of the first reaction vessel, or part of the second reaction vessel, or a separate vessel that is independent of the first and second reaction vessel.

The apparatus may further comprise controls for delivery of the constituents into and out of the vessels, controls for regulating temperature, pH and other physical reaction conditions, and a computer for controlling one or more aspects of the overall apparatus.

Certain processes of the invention are illustrated in the following examples. While multiple embodiments are disclosed herein, still other embodiments of the present invention may become apparent to those skilled in the art from review of the entirety of this specification. As should be realized from the description herein, the invention is capable of modifications in various aspects, all without departing from the spirit and scope of the present invention. Accordingly, the drawing and entirety of the description are to be regarded as illustrative in nature and not in a limiting sense.

Example 1

Production of $HIS_6$-HEXaspC aminotransferase in a Fed-Batch Fermentation

Materials

Bacterial growth media components were from Difco, Fisher Scientific, or VWR; other reagents were of analytical grade or the highest grade commercially available. The fermentation was run in a New Brunswick Scientific (Edison, N.J.) BioFlo 3000® fermenter. Centrifugation was carried out using a Beckman (Fullerton, Calif.) Avanti® J-25I centrifuge with a JLA-16.250 or JA-25.50 rotor.

The cloning of the gene encoding a derivative of *E. coli* aspC aminotransferase containing six changes in the coding sequence (HEXaspC) is described in U.S. Patent Publication No. 2005/0282260, incorporated herein by reference. The enzyme was first described by Onuffer and Kirsch et al. (*Protein Science* 4: 1750-1757 (1995)). The amino acid changes resulted in an enzyme with broader substrate specificity than the original enzyme, showing increased activity for aromatic amino acids.

The aminotransferase HEXaspC carrying an amino-terminal $HIS_6$-purification tag was produced in a fermentor at the 2.5-L scale, in a fed-batch process that achieves high cell densities and high levels of expression of the desired protein. The protocol and results for growth of *E.coli* strain BL21 (DE3)::HEXaspCpET30(Xa/LIC) are described as follows: Starting from a fresh culture plate (LB agar with 0.05 mg/mL kanamycin), the cells were grown in 5 mL of Luria-Bertani broth (LB) with 0.05 mg/mL kanamycin, at 37° C. and 225 rpm for 6-8 h. One mL of the culture was transferred to each of 2, 100-mL aliquots of the same medium and the cells were grown at 37° C. and 225 rpm overnight (16-18 h). A fermentor with 2.5 liters of medium containing (per liter): 2.0 g/L $(NH_4)_2SO_4$; 8.0 g/L $K_2HPO_4$; 2.0 g/L NaCl; 1.0 g/L $Na_3Citrate.2H_2O$; 1.0 g/L $MgSO_4.7H_2O$; 0.025 g/L $CaCl_2.2H_2O$; 0.05 g/L $FeSO_4.7H_2O$; 0.4 ml/L Neidhardt micronutrients, 2.0 g/L glucose and 0.5 mg/mL kanamycin was inoculated with 5% v/v (volume per volume) of the overnight culture. Two hours after inoculation, an exponential glucose feed was set up using a 60% w/v (weight per volume) glucose solution. The feed was supplied at the required rate to support microbial growth at an exponential rate of 0.15 $h^{-1}$. When the carbon dioxide evolution rate (CER) had reached a value of 100 mmoles/L/h (approximately 20 hours after inoculation, corresponding to a cell biomass of 15-16 g DCW/L), the gene expression was induced with a bolus addition of 2 g/L lactose (fed as a 20% solution). The feed was changed from 60% w/v glucose to 50% w/v glucose+10% w/v lactose while the feed rate was fixed to the rate at time of induction. The "50% w/v glucose+10% w/v lactose" feed was maintained for 6 hours. At the end of the fermentation, the cell concentration was 31 g DCW/L, with an estimated enzyme expression level of 38% of the total protein as calculated from the Bio-Rad (Hercules, Calif.) Experion™ system software (see below). The cells were harvested by centrifugation at 5000-7000×g for 10 min and frozen as a wet cell paste at −80° C.

Example 2

Purification of $HIS_6$-HEXaspC Aminotransferase

Cells were disrupted using a Microfluidics (Newton, Mass.) homogenizer. Protein expression was analyzed using a Bio-Rad (Hercules, Calif.) Experion™ Pro260 system or using Bio-Rad 4-15% SDS-polyacrylamide gradient gels run in a Mini PROTEAN® 3 cell apparatus. The protein was visualized in the gels using Bio-Rad Bio-Safe™ G-250 Coomassie stain and destained with water. The $HIS_6$-tagged enzyme was purified with GE Healthcare (Piscataway, N.J.) Chelating Sepharose™ Fast Flow resin. GE Healthcare PD10 columns were used for exchanging buffer in protein solutions. Protein solutions were concentrated with Millipore/Amicon (Billerica, Mass.) Centricon® Plus-70 centrifugal filter devices (MWCO (molecular weight cut-off) 10 kDa). Protein concentrations were determined using the Pierce (Rockford, Ill.) BCA™ assay kit with bovine serum albumin as the standard. Centrifugation was carried out in a Beckman (Fullerton, Calif.) Avanti® J-25I centrifuge with a JLA-16.250 or JA-25.50 rotor. All reagents were of analytical grade or the highest grade commercially available.

To prepare cell free extract containing the $HIS_6$-HEXaspC aminotransferase, the cells were suspended in 3-4 volumes of 100 mM potassium phosphate, pH 7.8, containing 0.05 mM pyridoxal phosphate (PLP) and then disrupted using a Microfluidics homogenizer (3 passes at 20,000 psi), maintaining the temperature of the suspension at less than 15° C. All subsequent purification steps were carried out at 4° C. The cell extract was centrifuged for 20 minutes at 15,000×g to remove the cell debris. A 20-25 mL aliquot of the cell free extract was applied to a 45 mL column of Chelating Sepharose™ Fast Flow resin (nickel(II) form) that had been previously equilibrated with 100 mM potassium phosphate containing 200 mM sodium chloride and 0.05 mM PLP. To generate the nickel form of the resin, the resin was washed with 150 mL of 200 mM nickel(II) sulfate hexahydrate and then with 150 mL of distilled water. After loading the sample, the column was washed/eluted with 150 mL of the equilibration buffer containing 25 mM imidazole, 150 mL of the equilibration buffer containing 50 mM imidazole and 150 mL of the equilibration buffer containing 500 mM imidazole. The $HIS_6$-HEXaspC protein eluted in the last wash. The 500 mM imidazole wash was concentrated with Centricon® Plus-70 centrifugal filter devices (MWCO 10 kDa) to 15-20 mL according to the manufacturer's instructions. The imidazole and sodium chloride were removed by passage through disposable PD10 columns (2.5 mL sample per column) previously equilibrated with 100 mM potassium phosphate, pH 7.8 containing 0.05 mM PLP. The purified aminotransferase was eluted with 3.5 mL per column of the same buffer. The protein concentration of each fraction was determined using the Pierce BCA™ assay kit. The purity of each fraction and the level of expression in the cell free extract fraction were determined using an Experion™ microcapillary chip system or by SDS-PAGE with 4-15% gradient gels. Typically this procedure produces ~150 mg of enzyme (from 600-700 mg of total protein) that is 85-90% pure as judged by the Experion™ software. Aliquots (1-5 mL) of the purified enzyme were stored at −80° C. until use.

Example 3

Expression and Purification of *Comamonas testosteroni* proA Aldolase

Materials

Cell growth and gene induction was carried out using Overnight Express™ System II (EMD Biosciences/Novagen; Madison, Wis.). All other materials were the same as those used in the purification of $HIS_6$-HEXaspC aminotransferase.

The cloning of the gene encoding a derivative of *C. testosteroni* proA aldolase is described in the U.S. Patent Publication No. 2004/0063175.

The proA aldolase with an amino-terminal $HIS_6$-purification tag was produced using Overnight Express™ System II (solutions 1-6) containing 0.05 mg/mL kanamycin in shake flasks. This expression system induces the expression of IPTG-inducible systems without the need to monitor cell growth. After inoculation of 200 mL aliquots of the medium (in 1 L flasks) from either liquid cultures or plates of BL21 (DE3)::*C. testosteroni* proA pET30(Xa/LIC), the cultures were incubated at 30° C. overnight with shaking at 225 rpm. When the $OD_{600}$ had reached a minimum of 6, the cells were harvested by centrifugation as described above.

Cell extracts with the expressed proA aldolase were prepared as described above using 100 mM potassium phosphate, pH 7.8 containing 200 mM NaCl as the suspension buffer. In some cases 4 mM $MgCl_2$ was also added to the buffer. The protein was purified as described above, loading cell extract prepared from the cells of 4 flasks onto a 45 mL Chelating Sepharose™ Fast Flow resin (nickel(II) form) column previously equilibrated with 100 mM potassium phosphate, pH 7.8 containing 200 mM NaCl. The protein eluted in the fraction containing 500 mM imidazole in the equilibration buffer. This fraction was concentrated as described above and the imidazole was removed by passage through PD10 columns equilibrated with 100 mM potassium phosphate, pH 7.8 with 200 mM sodium chloride and 4 mM $MgCl_2$. The protein concentration of each fraction was determined using the Pierce BCA™ assay. The purity of each fraction and the level of expression in the cell free extract fraction were determined using a BioRad Experion™ microcapillary chip system or by SDS-PAGE with 4-15% gradient gels. Typically this procedure produces more than 200 mg of enzyme that is 85-90% pure as judged by the Experion™ software. Aliquots (1-5 mL) of the purified enzyme were stored at −80° C. until use.

Example 4

Small Scale Biocatalytic Production of S,S-Monatin from Tryptophan and Pyruvate

Materials

All reagents were of analytical grade or the highest grade commercially available. The enzymes used to catalyze the formation of S,S-monatin were purified as described in Examples 2 and 3.

Methods and Results

A small-scale protocol was developed for the biocatalytic production of S,S-monatin from L-tryptophan and pyruvate. The enzyme reactions were carried out in 15 mL screw cap plastic tubes. A solution of 50 mM L-tryptophan, 200 mM pyruvate, 4 mM $MgCl_2$, 0.05 mM PLP in potassium phosphate, pH 7.8 was used in the standard protocol and the tubes containing this solution were incubated at room temperature with gentle mixing. Enzyme solutions were added to a concentration of 0.05 g/L for the purified *Comamonas testosteroni* proA aldolase and 0.5 g/L for the $HIS_6$-HEXaspC aminotransferase to initiate the reactions (10 mL final volume). The final concentration of potassium phosphate was 25 mM, including the buffer contribution from the enzyme solutions. Additions of the detergents Tween 80® and Triton® X-100 (0.01-1%) minimized precipitation of the enzymes. The reactions proceeded quickly after the enzyme addition and the rates decreased over time. At 3-5 h, a second aliquot of 50 mM L-tryptophan was added and the reactions were continued for up to 24 h. The progress of the reactions was followed by measuring L-tryptophan, L-alanine, monatin, monatin precursor (2-hydroxy-2-(1H-indol-3-ylmethyl)-4-oxo-pentanedioic acid) and pyruvic acid concentrations. Monatin, tryptophan, and alanine concentrations were measured using the fluorescence-post column derivatization protocol described in Example 6. Monatin precursor and pyruvate analytical methods are described in Example 6. Typical results from experiments at the 10 mL scale are shown in Table 1.

TABLE 1

Small scale production of S,S-monatin

| Detergent | [S,S-monatin]; mM |
|---|---|
| None | 3.6 |
| 0.01% Tween® 80 | 11.4 |
| 0.1% Tween® 80 | 12.5 |
| 0.1% Triton® X-100 | 11.8 |

Example 5

Bench-Scale Improved Biocatalytic Production of S,S-Monatin from Tryptophan and Pyruvate Materials All reagents were of analytical grade or the highest grade commercially available. The enzymes used to catalyze the formation of S,S-monatin were purified as described in Examples 2 and 3. The bench-scale biocatalytic reactions were run in INFORS (Bottmingen, Switzerland) 0.7 L bioreactors. Protein was removed from the reaction mixtures using an Amicon (Millipore; Billerica, Mass.) ultrafiltration stirred cell (Model 8200) with a YM10 membrane or using a Millipore Pellicon® 50 cm$^2$ ultrafiltration cartridge (MWCO 10,000).

Methods and Results

The bench-scale biocatalytic reactions were carried out in 0.7 L reactors with temperature, pH, and agitation control. The oxygen catalyzed degradation of the intermediate indole-3-pyruvate was minimized by running the reactions in a nitrogen atmosphere.

Mixture I (First Reaction mixture): Solutions of 50 mM L-tryptophan, 200 mM pyruvate, 4 mM MgCl$_2$, and 0.05 mM PLP in potassium phosphate, pH 7.8 (300 mL) were prepared in the reactors; the temperature was controlled at 30° C. and the agitation rate at 250 rpm. Nitrogen was supplied either in the headspace of the reactors or was sparged into the liquid to minimize the oxygen concentration of the reaction solution. The pH was monitored and ranged from 7.5 to 7.8 during the course of the reaction. In some experiments, the detergent Tween® 80 was added to minimize precipitation of the enzymes. Enzyme solutions were added to a concentration of 0.05 g/L for the purified *Comamonas testosteroni* proA aldolase and 0.5 g/L for the HIS$_6$-HEXaspC aminotransferase to initiate the reactions. The final concentration of potassium phosphate was 25 mM, including the buffer contribution from the enzyme solutions. At 3-5 h, a second aliquot of 50 mM L-tryptophan was added to the reactors. The progress of the reactions was followed by measuring L-tryptophan, L-alanine, monatin, monatin precursor (2-hydroxy-2-(1H-indol-3-ylmethyl)-4-oxo-pentanedioic acid) and pyruvic acid concentrations. For tryptophan, monatin, and alanine the fluorescence post-column derivatization method was utilized. The concentration of indole-3-pyruvate was analyzed using the arsenate-borate spectrophotometric method. This method is not quantitative but allows the qualitative monitoring of the loss or formation of indole-3-pyruvate. All analytical methods are described in Example 6.

Ultrafiltration: After overnight incubation (18-24 h) the protein was removed from the reaction mixtures by ultrafiltration. The reaction mixtures were transferred anaerobically to an ultrafiltration stirred cell and the deproteinized solution was collected in a closed bottle that had been previously purged of oxygen with nitrogen. A blanket of nitrogen was maintained in the bottle during the ultrafiltration step. An aliquot of the deproteinized reaction solution (200 mL) was then transferred anaerobically to a 0.7 L fermentor. Alternatively, a Pellicon® ultrafiltration cartridge was used to deproteinize the reaction mixture by recirculation of the reaction mixture through the cartridge and collection of the permeate in a second closed, nitrogen purged 0.7 L reactor.

Mixture 2 (Second Reaction mixture): To the deproteinized solution was added an excess of L-alanine (to bring the initial concentration of L-alanine to 0.5 M or 1.5 M as shown in Table 2, below) and 0.5 g/L of purified HIS$_6$-HEXaspC aminotransferase. The temperature was maintained at 30° C., the pH between 7.5 and 7.8, and the agitation rate at 250 rpm. Nitrogen was supplied in the headspace continuously to maintain an anaerobic environment. The progress of the reaction was followed by measuring L-tryptophan, L-alanine, monatin, monatin precursor (2-hydroxy-2-(1H-indol-3-ylmethyl)-4-oxo-pentanedioic acid) and pyruvic acid concentrations. The loss of indole-3-pyruvate was analyzed using the arsenate-borate spectrophotometric method as described in Example 6. The results of typical reactions are shown in Table 2.

TABLE 2

Bench-scale production of S,S-monatin

| [Tween] | [Alanine] Added to Mixture 2 mM | Mixture 1 final concentrations | | | Mixture 2 final concentrations | | | Fold Increase in [Monatin] |
|---|---|---|---|---|---|---|---|---|
| | | [Monatin] mM | [Tryptophan] mM | [Monatin Precursor] mM | [Monatin] mM | [Tryptophan] mM | [Monatin Precursor] mM | |
| None | 500 | 14.8 | 27.1 | 13.6 | 20.2 | 48.6 | 9.3 | 1.4 |
| None | 1500 | 14.8 | 27.1 | 13.6 | 24.7 | 52.0 | 5.8 | 1.7 |
| 0.01% | 1500 | 14.6 | 27.9 | 14.0 | 21.3 | 47.7 | 1.8 | 1.5 |
| 0.1% | 1500 | 14.7 | 16.9 | 8.4 | 22.6 | 55.0 | 1.5 | 1.5 |

The results of Table 2 show that the formation of S,S-monatin can be increased up to 1.7-fold when an excess of an amino group donor (L-alanine) and the aminotransferase enzyme are added to the deproteinized reaction mixture 1. Much of the monatin precursor present in the reaction 1 mixtures was aminated to form monatin under these conditions while the indole-3-pyruvate was converted to the more stable tryptophan (as shown in Table 2 by the increase in tryptophan concentration). The increase in monatin titer with the bench-scale process compared to the small scale for reaction 1 is at least partly due to the exclusion of oxygen from the reaction mixtures and the increase in reaction temperature. Though the addition of detergent minimizes the precipitation of the proteins in both the small- and bench-scale processes, there was not the significant increase in product concentration in the larger reactions when detergent was present as was observed with the small-scale process.

Example 6

Detection of Monatin, Monatin Precursor, Tryptophan, Alanine, Pyruvate, HMO, HMG, and Indole-3-Pyruvate LC/MS/MS Multiple reaction Monitoring (MRM) Analysis of Monatin and Tryptophan Analyses of mixtures for monatin and tryptophan derived from biochemical reactions were performed using a Waters/Micromass® liquid chromatography-tandem mass spectrometry (LC/MS/MS) instrument including a Waters 2795 liquid chromatograph with a Waters 996 Photo-Diode Array (PDA)

absorbance monitor placed in series between the chromatograph and a Micromass® Quattro Ultima® triple quadrupole mass spectrometer. LC separations were made using an Xterra MS C8 reversed-phase chromatography column, 2.1 mm×250 mm at 40° C. The LC mobile phase consisted of A) water containing either (i) 0.05% (v/v) trifluoroacetic acid or (ii) 0.3% formic acid and 10 mM ammonium formate and B) methanol containing either (i) 0.05% (v/v) trifluoroacetic acid or (ii) 0.3% formic acid and 10 mM ammonium formate.

If the LC mobile phase consisted of A) water containing 0.05% (v/v) trifluoroacetic acid and B) methanol containing 0.05% (v/v) trifluoroacetic acid, gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 2 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]+) of the analytes of interest, and production of characteristic fragment ions. The following instrumental parameters were used for LC/MS/MS Multiple Reaction Monitoring (MRM) analysis of monatin and tryptophan: Capillary: 3.5 kV; Cone: 40 V; Hex 1:20 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 8; Exit: 1 V; Low mass resolution (Q2): 15; High mass resolution (Q2): 15; Ion energy (Q2): 3.5; Multiplier: 650. Five monatin-specific parent-to daughter MRM transitions are used to specifically detect monatin in in vitro reactions. The transitions monitored are 293.1 to 158.3, 293.1 to 168.2, 293.1 to 211.2, 293.1 to 230.2, and 293.1 to 257.2. Tryptophan is monitored with the MRM transition 204.7 to 146.4. For internal standard quantification of monatin and tryptophan, four calibration standards containing four different ratios of each analyte to $d_5$-tryptophan and $d_5$-monatin, are analyzed. These data are subjected to a linear least squares analysis to form a calibration curve for monatin and tryptophan. To each sample is added a fixed amount of $d_5$-tryptophan and $d_5$-monatin ($d_5$-monatin was synthesized from $d_5$-tryptophan according to the methods from WO 2003/091396 A2), and the response ratios (monatin/$d_5$-monatin; tryptophan/$d_5$-tryptophan) used in conjunction with the calibration curves described above to calculate the amount of each analyte in the mixtures.

If the LC mobile phase was A) water containing 0.3% formic acid and 10 mM ammonium formate and B) methanol containing 0.3% formic acid and 10 mM ammonium formate, the gradient elution was linear from 5% B to 45% B, 0-8.5 min, linear from 45% B to 90% B, 8.5-9 min, isocratic from 90% B to 90% B, 9-12.5 min, linear from 95% B to 5% B, 12.5-13 min, with a 4 min re-equilibration period between runs. The flow rate was 0.27 mL/min, and PDA absorbance was monitored from 210 nm to 400 nm. All parameters of the ESI-MS were optimized and selected based on generation of protonated molecular ions ([M+H]+) of the analytes of interest, and production of characteristic fragment ions. The instrumental parameters used for this secondary mobile phase are the same as above. Four monatin-specific parent-to-daughter MRM transitions and one tryptophan specific parent-to-daughter transition are used to specifically detect monatin and tryptophan in in vitro and in vivo reactions. The transitions monitored are 293.1 to 158.0, 293.1 to 168.0, 293.1 to 211.5, and 293.1 to 257.0. Tryptophan is monitored with the MRM transition 205.2 to 146.1. For internal standard quantification of monatin and tryptophan, four calibration standards containing four different ratios of each analyte to $d_5$-tryptophan and $d_5$-monatin, are analyzed. These data are subjected to a linear least squares analysis to form a calibration curve for monatin and tryptophan. To each sample is added a fixed amount of $d_5$-tryptophan and $d_5$-monatin ($d_5$-monatin was synthesized from $d_5$-tryptophan according to the methods from WO 2003/091396 A2), and the response ratios (monatin/$d_5$-monatin; tryptophan/$d_5$-tryptophan) in conjunction with the calibration curves described above are used to calculate the amount of each analyte in the mixtures. Parent-to-daughter mass transitions monitored for $d_5$-tryptophan and $d_5$-monatin are 210.2 to 151.1, and 298.1 to 172.0 respectively.

Chiral LC/MS/MS (MRM) Measurement of Monatin

Determination of the stereoisomer distribution of monatin in biochemical reactions was accomplished by derivitization with 1-fluoro-2-4-dinitrophenyl-5-L-alanine amide (FDAA), followed by reversed-phase LC/MS/MS MRM measurement.

Derivitization of Monatin with FDAA

To 50 μL of sample or standard was added 200 μL of a 1% solution of FDAA in acetone. 40 μL of 1.0 M sodium bicarbonate was added, and the mixture was incubated for 1 h at 40° C. with occasional mixing. The sample was removed and cooled, and neutralized with 20 μL of 2.0 M HCl (more HCl may be required to effect neutralization of a buffered biological mixture). After degassing was complete, samples were ready for analysis by LC/MS/MS.

LC/MS/MS Multiple Reaction Monitoring for the Determination of the Stereoisomer Distribution of Monatin Analyses were performed using the LC/MS/MS instrumentation described in the previous sections. The LC separations capable of separating all four stereoisomers of monatin (specifically FDAA-monatin) were performed on a Phenomenex Luna® 2.0×250 mm (3 μm) C18 reversed phase chromatography column at 40° C. The LC mobile phase consisted of A) water containing 0.05% (mass/volume) ammonium acetate and B) acetonitrile. The elution was isocratic at 13% B, 0-2 min, linear from 13% B to 30% B, 2-15 min, linear from 30% B to 80% B, 15-16 min, isocratic at 80% B 16-21 min, and linear from 80% B to 13% B, 21-22 min, with a 8 min re-equilibration period between runs. The flow rate was 0.23 mL/min, and PDA absorbance was monitored from 200 nm to 400 nm. All parameters of the ESI-MS were optimized and selected based on generation of protonated molecular ions ([M−H]−) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1:10 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5 V; Collision Energy: 20; Exit: 1 V; Low mass resolution (Q2): 12; High mass resolution (Q2): 12; Ion energy (Q2): 3.0; Multiplier: 650. Three FDAA-monatin-specific parent-to-daughter transitions were used to specifically detect FDAA-monatin in in vitro and in vivo reactions. The transitions were 543.6 to 268.2, 543.6 to 499.2, and 543.6 to 525.2. Identification of FDAA-monatin stereoisomers was based on chromatographic retention time as compared to purified monatin stereoisomers, and mass spectral data.

Liquid Chromatography-Post Column Fluorescence Detection of Amino Acids, Including Tryptophan, Monatin, Alanine, and HMG Procedure for Trytophan, Monatin, and Alanine Liquid chromatography with post-column fluorescence detection for the determination of amino acids in biochemical reactions was performed on a Waters 2690 LC system or equivalent combined with a Waters 474 scanning fluorescence detector, and a Waters post-column reaction module (LC/OPA method). The LC separations were performed on an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 min, isocratic at 100% B, 20-30 min, and linear from 100% B to 0% B, 30-31 min, with a 20 min re-equilibration period between runs. The flow rate for the mobile phase was 0.5 mL/min. The flow rate for the OPA post-column derivatization solution was 0.5 mL/min. The fluorescence detector settings were EX 338 nm and Em 425 nm. Norleucine was employed as an internal standard for the analysis. Identification of amino acids was based on chromatographic retention time data for purified standards.

Procedure for HMG

Samples from biochemical reactions were cleaned up by solid phase extraction (SPE) cartridges containing C18 as the packing material and 0.6% acetic acid as the eluent. The collected fraction from SPE was then brought up to a known volume and analyzed using HPLC post-column O-Phthaladehyde (OPA) derivatization with a florescensce detector. Chromatographic separation was made possible using a Waters 2695 liquid chromatography system and two Phenomenex AquaC18 columns in series; a 2.1 mm×250 mm column with 5 µm particles, and a 2.1 mm×150 mm column with 3 µm particles. The temperature of the column was 40° C. and the column isocratic flow rate was 0.18 mL/min. The mobile phase was 0.6% acetic acid. OPA post-column derivatization and detection system consists of a Waters Reagent Manager (RMA), a reaction coil chamber, a temperature control module for the reaction coil chamber, and a Waters 2847 Florescent detector. The OPA flow rate was set at 0.16 ml/min, and the reaction coil chamber was set to 80° C. The florescensce detector was set with an excitation wavelength of 348 nm and an emission wavelength of 450 nm. Other parameters controlling detector sensitivity, such as signal gain and attenuation, were set to experimental needs. Quantification of HMG was based off of the molar response of glutamic acid.

Detection of Monatin (2-hydroxy-2-(1H-indol-3-ylmethyl)-4-aminoglutaric acid) and Tryptophan by LC-UV/Vis Liquid chromatography separations were made using Waters 2690 liquid chromatography system and a 2.1 mm×150 mm Agilent Eclipse XDB-C18 5.0 µm reversed-phase chromatography column with flow rate at 0.22 ml/min and gradient conditions as follows:

| Time (min) | A % | B % |
|---|---|---|
| 0.0 | 95 | 5 |
| 4.5 | 40 | 60 |
| 11.0 | 5 | 95 |
| 11.5 | 95 | 5 |
| 20.0 | 95 | 5 |

The mobile phase A is 0.3% (v/v) formic acid with 10 mM ammonium formate, and mobile phase B is 0.3% (v/v) formic acid with 10 mM ammonium formate in 50/50 (v/v) methanol/acetonitrile. The column temperature was 40° C. Detection was performed using a Waters 996 Photodiode Array (PDA) operating at 280 nm. Typically a calibration range of 10-500 ppm is used.

Detection of Monatin Precursor (2-hydroxy-2-(1H-indol-3-ylmethyl)-4-oxo-pentanedioic acid) by LC/MS Liquid chromatography separations were made using Waters 2690 liquid chromatography system and a 2.1 mm×50 mm Agilent Eclipse XDB-C18 1.8 µm reversed-phase chromatography column with flow rate at 2.5 mL/min and gradient conditions as follows:

| Time (min) | A % | B % |
|---|---|---|
| 0.00 | 95 | 5 |
| 0.2 | 95 | 5 |
| 1.2 | 5 | 95 |
| 4.5 | 5 | 95 |
| 5.0 | 95 | 5 |
| 10 | 95 | 5 |

The mobile phase A is 0.3% (v/v) formic acid with 10 mM ammonium formate, and mobile phase B is 0.3% formic acid w/10 mM ammonium formate in 50:50 methanol/acetonitrile. The column temperature was 40° C.

Parameters for the Micromass ZQ quadrupole mass spectrometer operating in negative electrospray ionization mode (−ESI) were set as follows: Capillary: 2.2 kV; Cone: 35 V; Extractor: 4 V; RF lens: 1 V; Source temperature: 120° C.; Desolvation temperature: 380° C.; Desolvation gas: 600 L/h; Cone gas: Off; Low mass resolution: 15.0; High mass resolution: 15.0; Ion energy: 0.2; Multiplier: 650. Single ion monitoring MS experiment was set up to allow detection selectively for m/z 290.3, 210.3, 184.3, and 208.4. The m/z 208.4 is the deprotonated molecular [M−H]⁻ ion of the internal standard $d_5$-tryptophan.

Detection of Monatin Precursor by LC/MS/MS

LC separations were made using Waters HPLC liquid chromatography system and a 2.1 mm×50 mm Agilent Eclipse XDB-C18 1.8 µm reversed-phase chromatography column with flow rate at 0.25 mL/min and gradient conditions are as follows:

| Time (min) | A % | B % |
|---|---|---|
| 0.00 | 95 | 5 |
| 0.7 | 95 | 5 |
| 3.0 | 5 | 95 |
| 4.0 | 5 | 95 |
| 4.3 | 95 | 5 |
| 6.0 | 95 | 5 |

Mobile phase A is 0.3% (v/v) formic acid with 10 mM ammonium formate, and B is 0.3% formic acid with 10 mM ammonium formate in 50:50 methanol/acetonitrile. The column temperature was 40° C.

Parameters on Waters Premier XE triple quadrupole mass spectrometer for LC/MS/MS Multiple Reaction Monitoring (MRM) experiments operating in negative electrospray ionization mode (−ESI) were set as the following; Capillary: 3.0 kV; Cone: 25 V; Extractor: 3 V; RF lens: 0 V; Source temperature: 120° C.; Desolvation temperature: 350° C.; Desolvation gas: 650 L/hr; Cone gas: 47 L/hr; Low mass resolution (Q1): 13.5; High mass resolution (Q1): 13.5; Ion energy (Q1): 0.5 V; Entrance: 1 V; Collision Energy: 18 V; Exit 1: 19; Low mass resolution (Q2): 15; High mass resolution (Q2): 15; Ion Energy (Q2): 2.0; Multiplier: 650. Four parent-to-daughter MRM transitions were monitored to selectively detect Monatin precursor (MP) and $d_5$-Monatin precursor ($d_5$-MP); $d_5$-MP was used as an internal standard (I.S.). The four MRM transitions were 290.1 to 184.1, 290.1 to 210.1, 290.1 to 228.1, and 295.1 to 189.1. Two of these transitions, 290.1 to 184.1 for MP, and 295.1 to 189.1 for $d_5$-MP, were used for generating calibration curves and for quantification purposes. Transitions of 290.1 to 210.1 and 290.1 to 228.1 were used as qualitative secondary confirmation of MP.

Determination of Pyruvic Acid by HPLC with Refractive Index Detection

Pyruvic acid and other organic acids, such as α-ketoglutaric acid, were determined using a high performance liquid chromatography (HPLC) system with a refractive index detector. The system was comprised of a Waters 2690 and a Waters 2414 refractive index detector.

In some cases, separation of the compounds was made using an Aminex® HPX-87H, 300×7.8 mm ion exclusion column with isocratic elution at 35-60° C. The eluent was 0.01 N sulfuric acid in water and the flow rate was 0.5-0.6 mL/min. Samples to be analyzed were diluted in mobile phase to guarantee that the acids were in undissociated form. Samples were analyzed after filtration through 0.2 µm filters. The injection volume was 10 µL. A standard curve with good linearity was constructed for concentrations of pyruvic acid between 0.6 and 5 g/L for each acid.

In the Examples describing the downstream processes, liquid chromatography separations were made using Waters 2690 liquid chromatography system and two 4.6 mm×250 mm Restek Aqueous Allure—C18 5.0 µm reversed-phase chromatography columns with flow rate at 0.8 mL/min. The mobile phase was 50 mM phosphate buffer (pH 2.5 with phosphoric acid) and was run under isocratic conditions. The columns were held at a temperature of 50° C. The RI detector was run at 50° C. with a sensitivity setting of 32. A standard curve of 500-2500 ppm was used.

Detection of Indole-3-Pyruvate Using Sodium Tetraborate

This protocol measures the borate complex of the enol form of indole-3-pyruvate.

Standard solutions or reaction mixture samples containing indole-3-pyruvate (0.005 mL) were each added to 0.2 mL of 50 mM sodium tetraborate (pH 8.5) containing 0.5 mM EDTA and 0.5 mM sodium arsenate in 96-well microtiter plates. The microtiter plates are then incubated at 30° C. and the absorbance at 327 nm was measured. Because the color produced is not stable, all measurements were made exactly 30 min after the addition of the indole-3-pyruvate solutions. Indole-3-pyruvate from 0 to 10 mM dissolved in 100% ethanol was used for the standard curve. These solutions were stored at −20° C. between assays.

HMO Analysis Using Hydroxylamine Derivatization Method and UPLC/MS

HMO analysis was conducted by first removing an aliquot from a pre-diluted biochemical reaction sample, and then subsequently derivatizing by employing p-nitrobenzyl hydroxylamine (NBHA) hydrochloride (prepared in pyridine) for 25 min in a sonicating room temperature water bath. After the derivatization process was complete, the reaction mixture was further diluted with water to a known volume and subjected to ultra performance liquid chromatography mass spectrometry (UPLC/MS). Included in the UPLC/MS system was a photo diode array (PDA) detector, set to monitor the 260 nm to 499 nm wavelength region. LC separations were made using the aforementioned Waters UPLC system and a 2.1 mm×100 mm Agilent Eclipse XDB-$C_{18}$ 1.8 µm reversed-phase chromatography column set to a flow rate of 0.24 ml/min and employing the gradient conditions as follows:

| Time (min) | A %* | B %* |
|---|---|---|
| 0.00 | 87 | 13 |
| 0.20 | 87 | 13 |
| 5.50 | 50 | 50 |
| 6.50 | 30 | 70 |
| 11 | 30 | 70 |
| 11.3 | 87 | 13 |
| 15.00 | 87 | 13 |

*Mobile phase A was 0.3% (v/v) formic acid w/ 10 mM ammonium formate, and B was 0.3% formic acid w/ 10 mM ammonium formate in 50:50 MeOH/acetonitrile. The column temperature was 45° C.

Parameters on the Waters Premier XE triple quadrupole mass spectrometer for LC/MS scan mode experiment operating in negative electrospray ionization mode (−ESI) were set as follows: Capillary: 3.0 kV; Cone: 25 V; Extractor: 3 V; RF lens: 0 V; Source temperature: 120° C.; Desolvation temperature: 350° C.; Desolvation gas: 650 L/Hr; Cone gas: 47 L/Hr; Low mass resolution (Q1): 13.5; High mass resolution (Q1): 13.5; Ion energy (Q1): 0.5 V; Entrance: 30 V; Collision Energy: 3 V; Exit 1:30; Low mass resolution (Q2): 15; High mass resolution (Q2): 15; Ion Energy (Q2): 2.0; Multiplier: 650. A mass scanning range of 120 m/z to 1000 m/z MS method was used for qualitative identification of HMO-NBHA and 2-oxoglutamic-NBHA derivatives. Quantification of HMO-NBHA was based off of the molar response of 2-oxoglutamic-NBHA derivative measured at a wavelength of 275 nm.

Example 7

Expression and Purification of *B. sphaericus* D-alanine aminotransferase

Cell growth and gene induction was carried out using Overnight Express System II (EMD Biosciences/Novagen; Madison, Wis.). All other materials were the same as those used in the purification of $HIS_6$-HEXaspC aminotransferase.

The cloning of the gene encoding *B. sphaericus* D-alanine aminotransferase is described in the U.S. Patent Publication No. 2006/0252135, herein incorporated by reference, in Example 20.

The *B. sphaericus* D-alanine aminotransferase with an amino-terminal $HIS_6$-purification tag was produced using Overnight Express System II (solutions 1-6) containing 50 µg/mL kanamycin in shake flasks. This expression system induces the expression of IPTG-inducible systems without the need to monitor cell growth. After inoculation of 200 mL aliquots of the medium (in 1 L flasks) from either liquid cultures or glycerol stocks of BL21(DE3):: *B. sphaericus* dat pET30a the cultures were incubated at 30° C. overnight with shaking at 225 rpm. When the $OD_{600}$ was greater than 6, the cells were harvested by centrifugation in a Beckman (Fullerton, Calif.) J2511 centrifuge with a JS-16.25 rotor at 10,000 rpm for 10 minutes. The cell pellet was washed once with cold buffer and the cells were centrifuged again. The washed cell pellet was harvested and used immediately or frozen at −80°

C. until needed for purification. To prepare cell-free extract containing the *B. sphaericus* HIS$_6$-D-alanine aminotransferase (HIS$_6$-BsphDAT) protein, the cells were suspended in 3-4 volumes of 50 mM potassium phosphate, pH 7.8 containing 50 µM PLP, and then disrupted using a Microfluidics (Newton, Mass.) homogenizer (3 passes at 20,000 psi), maintaining the temperature of the suspension below 15° C. Alternatively, cell extracts were prepared using Novagen Bug-Buster (primary amine-free) Extraction Reagent (EMD Bioscience; Madison, Wis.) containing 1 µL/mL BenzonaseR Nuclease (EMD Bioscience), 5 µL/mL Protease Inhibitor Cocktail Set II (EMD Bioscience), and 0.33 µL/mL rLysozyme™ (EMD Bioscience) following the manufacturer's protocol. In either case, the cell debris was removed by centrifugation in a Beckman J2511 centrifuge with a JS-25 rotor at 15,000 rpm for 30 minutes, producing the cell free extract. All subsequent purification steps of the HIS$_6$-tagged protein were carried out at 4° C. The cell free extract from 600 mL of Overnight Express II culture was applied to 2 40-45 mL columns containing GE Healthcare (Piscataway, N.J.) Chelating Sepharose™ Fast Flow resin (nickel(II) form) that had been previously equilibrated with 100 mM potassium phosphate, pH 7.8, containing 200 mM sodium chloride and 50 µM PLP. After loading the sample, the columns were washed/eluted successively with 3-5 volumes of the equilibration buffer, 3-5 volumes of the equilibration buffer containing 25 mM imidazole, 3-5 volumes of the equilibration buffer containing 50-100 mM imidazole and 3-5 volumes of the equilibration buffer containing 500 mM imidazole. The HIS$_6$-BsphDAT protein eluted in the last wash. The 500 mM imidazole wash was concentrated with an Amicon (Billerica, Mass.) Centricon-70 or Ultra-15 centrifugal filter device (MWCO 10 kDa). The imidazole and sodium chloride were removed by passage through disposable GE Healthcare PD10 desalting columns previously equilibrated with 100 mM potassium phosphate, pH 7.8, containing 50 µM PLP. The protein concentration of the desalted solution was determined using the Pierce BCA assay kit (Rockford, Ill.). The purity of each fraction and the level of expression in the cell free extract fraction were determined using a Bio Rad (Hercules, Calif.) Experion Pro260 microcapillary chip system or by SDS-PAGE with 4-15% gradient gels. Typically this procedure produces more than 300 mg of enzyme (from 600 mL of Overnight Express II culture) that is ~90% pure as judged by the Experion software. Aliquots (1-5 mL) of the purified enzyme were stored at −80° C. until use.

Example 8

Expression and Purification of Aldolase

Materials

Cell growth and gene induction was carried out using Overnight Express System II (EMD Biosciences/Novagen; Madison, Wis.). All other materials were the same as those used in the purification of HIS$_6$-HEXaspC aminotransferase.

The cloning of the gene encoding the aldolase is described in U.S. Patent Publication No. 2006/0252135 in Example 3, which is herein incorporated by reference in it entirety (the aldolase as referred herein correlates to SEQ ID NO:22 of the reference).

The aldolase with an amino-terminal HIS$_6$-purification tag was produced using Overnight Express System II (solutions 1-6) containing 50 µg/mL kanamycin in shake flasks. This expression system induces the expression of IPTG-inducible systems without the need to monitor cell growth. After inoculation of 200 mL aliquots of the medium (in 1 L flasks) from either liquid cultures or glycerol stocks of the construct, the cultures were incubated at 30° C. overnight with shaking at 225 rpm. When the OD$_{600}$ was greater than 6, the cells were harvested by centrifugation in a Beckman (Fullerton, Calif.) J25II centrifuge with a JS-16.25 rotor at 10,000 rpm for 10 minutes. The cell pellet was washed once with cold buffer and the cells were centrifuged again. The washed cell pellet was harvested and used immediately or frozen at −80° C. until needed for purification. Cell-free extracts containing the HIS$_6$-tagged aldolase were prepared using Novagen Bug-Buster (primary amine-free) Extraction Reagent (EMD Bioscience; Madison, Wis.) containing 1 µL/mL BenzonaseR Nuclease (EMD Bioscience), 5 µL/mL Protease Inhibitor Cocktail Set II (EMD Bioscience), and 0.33 µL/mL rLysozyme™ (EMD Bioscience) following the manufacturer's protocol. The cell debris was removed by centrifugation in a Beckman J2511 centrifuge with a JS-25 rotor at 15,000 rpm for 30 minutes, producing the cell free extract. All subsequent purification steps of the HIS$_6$-tagged protein were carried out at 4° C. The cell free extract from 800 mL of Overnight Express II culture was applied to a column of GE Healthcare (Piscataway, N.J.) Chelating Sepharose™ Fast Flow resin (nickel(II) form) that had been previously equilibrated with 100 mM potassium phosphate, pH 7.8, containing 200 mM sodium chloride. After loading the sample, the column was washed/eluted successively with 3-5 volumes of the equilibration buffer, 3-5 volumes of the equilibration buffer containing 25 mM imidazole, 3-5 volumes of the equilibration buffer containing 50-100 mM imidazole and 3-5 volumes of the equilibration buffer containing 500 mM imidazole. The HIS$_6$-tagged aldolase eluted in the last wash. The 500 mM imidazole wash was concentrated with an Amicon (Billerica, Mass.) Centricon-70 or Ultra-15 centrifugal filter devices (MWCO 10 kDa). The imidazole and sodium chloride were removed by passage through disposable GE Healthcare PD10 desalting columns previously equilibrated with 100 mM potassium phosphate, pH 7.8, containing 200 mM sodium chloride and 4 mM MgCl$_2$. The protein concentration of the desalted solution was determined using the Pierce BCA assay kit (Rockford, Ill.). The purity of each fraction and the level of expression in the cell free extract fraction were determined using a Bio Rad (Hercules, Calif.) Experion Pro260 microcapillary chip system or by SDS-PAGE with 4-15% gradient gels. Typically this purification procedure produces 18-20 mg of enzyme (from 800 mL of Overnight Express II culture) that is 85-90% pure as determined by the Experion software. Aliquots (1 mL) of the purified enzyme were stored at −80° C. until us.

Example 9

Small Scale Biocatalytic Production of R,R-Monatin from D-Tryptophan and Pyruvate Using 2 Reaction Steps Materials All reagents were of analytical grade or the highest grade commercially available. The *B. sphaericus* HIS$_6$-tagged D-alanine aminotransferase and the HIS$_6$-tagged aldolase used to catalyze the formation of R,R-monatin were purified as described in Examples 7 and 8.

Methods and Results

A small-scale protocol was developed for the biocatalytic production of R,R-monatin from D-tryptophan and pyruvate that excludes oxygen from the reaction mixtures to minimize the oxygen catalyzed degradation of the intermediate indole-3-pyruvate. The enzyme reactions were carried out in 10-mL glass serum bottles with stoppers and aluminum seals.

Reaction 1: A solution of 200 mM sodium pyruvate, 4 mM $MgCl_2$, and 50 µM PLP in potassium phosphate, pH 7.8 was prepared in a 100 mL serum bottle. The bottle was stoppered and sealed, and then the liquid was purged with nitrogen for several minutes. Aliquots of this solution were anaerobically transferred to 10-mL serum bottles containing solid D-tryptophan. These 10-mL bottles had been previously closed with stoppers and aluminum seals and then purged with nitrogen. Enzyme solutions were added to a concentration of 0.05 g/L for the purified $HIS_6$-tagged aldolase and 0.5 g/L for the $HIS_6$-D-alanine aminotransferase to initiate the reactions (7 mL final volume). The final concentration of potassium phosphate was 25 mM, including the buffer contribution from the enzyme solutions. The final concentration of D-tryptophan was 100 mM. The reaction bottles were incubated at room temperature with gentle mixing, sampling 5 h and 20 h after the addition of the enzymes. The enzyme stabilization efficacy of the detergent Tween-80 was determined by adding this detergent at 0.1% and 0.01% to some of the reaction mixtures. The progress of the reactions was followed by measuring D-tryptophan, D-alanine, R,R-monatin, R-monatin precursor (2-hydroxy-2-(1H-indol-3-ylmethyl)-4-oxo-pentanedioic acid) and pyruvic acid. Tryptophan, alanine, and monatin concentrations were measured utilizing the fluorescence post-column derivatization method. All analytical methods are described in Example 6.

After overnight incubation the protein was removed from the reaction mixtures by ultrafiltration using Amicon Ultra-15 centrifugal filter devices (MWCO 10 kDa).

Reaction 2: The deproteinized solutions were added to 10-mL serum bottles containing solid D-alanine. These 10-mL bottles had been previously closed with stoppers and aluminum seals and then purged with nitrogen. The $HIS_6$-D-alanine aminotransferase was then added at a final concentration of 0.5 mg/mL to initiate the reactions (5 mL final volume). The final concentration of D-alanine was 1500 mM. The reaction bottles were incubated at room temperature with gentle mixing, sampling 4 h and 20 h after the addition of the enzyme. The progress of the reactions was followed by measuring D-tryptophan, D-alanine, R,R-monatin, R-monatin precursor (2-hydroxy-2-(1H-indol-3-ylmethyl)-4-oxo-pentanedioic acid), and pyruvic acid. Tryptophan, alanine, and monatin concentrations were measured utilizing the fluorescence post-column derivatization method. Pyruvate concentration was determined using the LC-RI method and an Aminex® column for separation. All analytical methods are described in Example 6.

Example 10

Immobilization of *B. sphaericus* D-alanine aminotransferase

The *Bacillus sphaericus* D-alanine aminotransferase was purified as the $HIS_6$-tagged protein as described in Example 7.

The enzyme was immobilized onto Eupergit® C250 L resin beads according to the procedure of Mateo et al (2002). To 48 mg of the purified enzyme (5.2 mL at 9.3 mg/mL) was added potassium phosphate to a final concentration of 0.5 M and pH of 7.8, pyridoxal phosphate (PLP) to a final concentration of 0.05 mM. The resulting solution was mixed with 0.4 g of Eupergit® C 250 L resin purchased from Sigma-Alrich (St. Louis, Mo.). The enzyme-resin suspension was incubated at ambient temperature with gentle mixing overnight. The resin beads were separated from the enzyme solution by centrifugation at 4000×g for 5 min. The supernatant was removed and the resin was washed with 3×5 mL of 100 mM potassium phosphate, pH 7.8 containing 0.05 mM PLP. The mixture was centrifuged at 4000×g for 5 min between washes. The amount of protein bound to the resin was determined by measuring the amount of protein in each wash and subtracting the sum from the original amount of protein to be immobilized. The protein concentrations were measured using a Pierce BCA™ Protein Assay Kit with bovine serum albumin as the standard (Rockford, Ill.). The washed immobilized-enzyme beads were finally suspended in 3 mL of 100 mM potassium phosphate, pH 7.8 containing 0.05 mM PLP. The unreacted epoxy groups of the immobilized-enzyme beads were blocked by incubation with 1.4 M glycine at ambient temperature with gentle mixing. After 24 h, the beads were washed with 4×10 mL of 50 mM EPPS, pH 8.4 containing 0.05 mM PLP to remove the excess glycine and were finally resuspended in 5 mL of 50 mM EPPS, pH 8.4 containing 0.05 mM PLP. The final concentration of immobilized enzyme was 66 mg protein per g resin bead.

Reference: Mateo, C., Abain, O., Fernandez-Lorente, G., Pedroche, J., Femandez-Lafuente, R., Guisan, J. M., Tam, A., and Daminati, M., *Biotechnology Progress* 18(3): 629-634 (2002).

Example 11

Cloning of the SEQ ID NO:1 Aldolase Gene that Encodes the Aldolase of SEQ ID NO:2

The gene encoding the aldolase of SEQ ID NO:2 (the DNA sequence of the gene is shown as SEQ ID NO:1) was sub-

TABLE 3

Small-scale production of R,R-monatin using 2 reaction steps to improve the monatin titer

| [Tween] | [Alanine] Added to Reaction 2 | Reaction 1 final concentrations | | | Reaction 2 final concentrations | | | Fold Increase in [Monatin] |
|---|---|---|---|---|---|---|---|---|
| | | [Monatin] mM | [Tryptophan] mM | [Monatin Precursor] mM | [Monatin] mM | [Tryptophan] mM | [Monatin Precursor] mM | |
| none | 1500 | 5.1 | 23.9 | 8.7 | 11.2 | 43.4 | 14.0 | 2.2 |
| 0.01% | 1500 | 4.9 | 26.4 | 9.0 | 10.7 | 46.2 | 14.2 | 2.2 |
| 0.1% | 1500 | 5.2 | 27.8 | 9.6 | 11.4 | 46.9 | 12.8 | 2.2 | cloned into the pET28b expression vector (EMD Biosciences/Novagen, Madison, Wis.) with an N-terminal His-tag to allow for purification of the enzyme. The gene was also cloned into pET30a (no tag).

The primers used for cloning are shown below:

```
                                              (SEQ ID NO:3)
5'-ATAAGACATATGCCTATCGTTGTTACGAAG-3'
(Nde I restriction site)
and
                                              (SEQ ID NO:4)
5'-ATAAGAGGATCCTTATTCCTCGGGCAGCCGCTC-3'
(BamH I restriction site).
```

A clone containing SEQ ID NO:1 was received from Diversa Corporation, San Diego, Calif., and used as a template for PCR. However, SEQ ID NO:1 can be reconstructed by other methods known to a person of ordinary skill in the art. For example, SEQ ID NO:1 can be reconstructed utilizing assembly PCR methods. SEQ ID NO:1 was amplified by PCR, digested with the restriction enzymes Nde I and BI, and purified from an agarose gel (QIAquick® Gel extraction Kit (Qiagen, Valencia, Calif.)). The digest was ligated into pET28b (EMD Biosciences/Novagen Madison, Wis.) and pET30a that had been digested with Nde I and BamH I and gel purified. The ligation was transformed into TOP10 E. coli cells (Invitrogen, Carlsbad, Calif.). Plasmid DNA from colonies was analyzed for the presence of inserts by size comparison using agarose gel electrophoresis. Isolates with an insert of the predicted size were submitted for DNA sequence analysis (Agencourt, Beverly, Mass.).

The DNA sequence of the gene SEQ ID NO: 1 that encodes the aldolase of SEQ ID NO:2 is shown below:

```
                                              (SEQ ID NO: 1)
atgcctatcg ttgttacgaa gatcgaccga cccagcgcgg
cggacgtcga aaggatcgcc gcctatggtg tcgcgacctt
gcatgaagcg caaggacgaa ccgggttgat ggcgtccaat
atgcgcccaa tctatcgccc tgcgcacatt gccgggcccg
cggtgacctg ccttgtggcg cctggcgaca attggatgat
ccatgtcgcc gtcgaacagt gccagccggg agatgtcctg
gtcgtggtac cgaccagccc ctgcgaagac ggctatttcg
gcgatctgct ggcgacctcg ctgcggtcgc gcggggtcaa
aggtctgatc atcgaggccg gcgtacgcga tatcgcgaca
ttgaccgaga tgaaattccc ggtctggtcc aaggcggtgt
tcgcgcaagg aacggtcaag gagaccatcg ccagcgtcaa
tgtgccccttc gtctgcgcgg gcgcccgcat cgtgccgggc
gatctgatcg ttgccgacga cgacggggtc gtcgtgattc
caagacgttc cgttccggcg gtcctttcca gcgccgaggc
ccgcgaagag aaggaagccc gcaaccgcgc ccgcttcgaa
gctggcgagc tgggcctcga cgtctacaac atgcgccagc
gcctggccga caagggcttg cgctatgtcg agcggctgcc
cgaggaatag.
```

The protein sequence of the aldolase of SEQ ID NO:2 is as follows:

```
                                              (SEQ ID NO:2)
Met Pro Ile Val Val Thr Lys Ile Asp Arg Pro Ser
Ala Ala Asp Val Glu Arg Ile Ala Ala Tyr Gly Val
Ala Thr Leu His Glu Ala Gln Gly Arg Thr Gly Leu
Met Ala Ser Asn Met Arg Pro Ile Tyr Arg Pro Ala
His Ile Ala Gly Pro Ala Val Thr Cys Leu Val Ala
Pro Gly Asp Asn Trp Met Ile His Val Ala Val Glu
Gln Cys Gln Pro Gly Asp Val Leu Val Val Val Pro
Thr Ser Pro Cys Glu Asp Gly Tyr Phe Gly Asp Leu
Leu Ala Thr Ser Leu Arg Ser Arg Gly Val Lys Gly
Leu Ile Ile Glu Ala Gly Val Arg Asp Ile Ala Thr
Leu Thr Glu Met Lys Phe Pro Val Trp Ser Lys Ala
Val Phe Ala Gln Gly Thr Val Lys Glu Thr Ile Ala
Ser Val Asn Val Pro Leu Val Cys Ala Gly Ala Arg
Ile Val Pro Gly Asp Leu Ile Val Ala Asp Asp Asp
Gly Val Val Val Ile Pro Arg Arg Ser Val Pro Ala
Val Leu Ser Ser Ala Glu Ala Arg Glu Glu Lys Glu
Ala Arg Asn Arg Ala Arg Phe Glu Ala Gly Glu Leu
Gly Leu Asp Val Tyr Asn Met Arg Gln Arg Leu Ala
Asp Lys Gly Leu Arg Tyr Val Glu Arg Leu Pro Glu
Glu.
```

Example 12

Purification of SEQ ID NO:2 Aaldolase

Cell growth and gene induction was carried out using Overnight Express System II (EMD Biosciences/Novagen; Madison, Wis.). All other materials were the same as those used in the purification of $HIS_6$-HEXaspC aminotransferase.

The cloning of the gene encoding the SEQ ID NO:2 aldolase is described in Example 11.

The SEQ ID NO:2 aldolase with an amino-terminal $HIS_6$-purification tag was produced using Overnight Express System II (solutions 1-6) containing 50 µg/mL kanamycin in shake flasks. After inoculation of 200 mL aliquots of the medium (in 1 L flasks) from either liquid cultures or glycerol stocks of the pET28b construct, the cultures were incubated at 30° C. overnight with shaking at 225 rpm. When the $OD_{600}$ was greater than 6, the cells were harvested by centrifugation in a Beckman (Fullerton, Calif.) J25II centrifuge with a JS-16.25 rotor at 10,000 rpm for 10 minutes. The cell pellet was washed once with cold buffer and the cells were centrifuged again. The washed cell pellet was harvested and used immediately or frozen at −80° C. until needed for purification. Cell-free extract containing the $HIS_6$-tagged SEQ ID NO:2 aldolase were prepared using Novagen BugBuster (primary amine-free) Extraction Reagent (EMD Bioscience; Madison, Wis.) containing 1 µL/mL Benzonase® Nuclease (EMD Bioscience), 5 μL/mL Protease Inhibitor Cocktail Set II (EMD Bioscience), and 0.33 μL/mL rLysozyme™ (EMD Bioscience) following the manufacturer's protocol. The cell debris were removed by centrifugation in a Beckman J25II centrifuge with a JS-25 rotor at 15,000 rpm for 30 minutes, producing the cell free extract. All subsequent purification steps of the $HIS_6$-tagged protein were carried out at 4° C. The cell free extract from 2×200 mL of Overnight Express II culture was applied to a column of GE Healthcare (Piscataway, N.J.) Chelating Sepharose™ Fast Flow resin (nickel(II) form) that had been previously equilibrated with 100 mM potassium phosphate, pH 7.8, containing 200 mM sodium chloride. After loading the sample, the column was washed/eluted successively with 3-5 volumes of the equilibration buffer containing 25 mM imidazole, 3-5 volumes of the equilibration buffer containing 50-100 mM imidazole and 3-5 volumes of the equilibration buffer containing 500 mM imidazole. The $HIS_6$-tagged SEQ ID NO:2 aldolase eluted in the last wash. The 500 mM imidazole wash was concentrated with an Amicon (Billerica, Mass.) Centricon-70 or Ultra-15 centrifugal filter devices (MWCO 10 kDa). The imidazole and sodium chloride were removed by passage through disposable GE Healthcare PD10 desalting columns previously equilibrated with 100 mM potassium phosphate, pH 7.8. The enzyme was less soluble (judged by cloudiness of the protein solution) after the desalting step if 4 mM $MgCl_2$, 200 mM NaCl, and/or 0.01% Tween-80 were added to the elution buffer. The protein concentration of the desalted solution was determined using the Pierce BCA assay kit (Rockford, Ill.). The purity of each fraction and the level of expression in the cell free extract fraction were determined using a Bio Rad (Hercules, Calif.) Experion Pro260 microcapillary chip system or by SDS-PAGE with 4-15% gradient gels. Typically this purification procedure produces about 50-80 mg of enzyme (from 400 mL of Overnight Express II culture) that is 85-90% pure as determined by the Experion software. Aliquots (1 mL) of the purified enzyme were stored at −80° C. until use.

Example 13

Immobilization of SEQ ID NO:2 Aldolase

The SEQ ID NO:2 aldolase was purified as the $HIS_6$-tagged protein as described in Example 12.

The enzyme was immobilized onto Eupergit® C resin beads according to the procedure of Mateo et al. (2002). To 20.4 mg of the purified enzyme (14.1 mL at 1.45 mg/mL) was added potassium phosphate to a final concentration of 0.5 M and pH of 7.8 and a final concentration of $MgCl_2$ of 1 mM. The resulting solution was mixed with 0.2 g of Eupergit® C 250 L resin purchased from Sigma-Aldrich (St. Louis, Mo.). The enzyme-resin suspension was incubated at ambient temperature with gentle mixing overnight. The resin beads were separated from the enzyme solution by centrifugation at 4000×g for 5 min. The supernatant was removed and the resin was washed with 3×5 mL of 100 mM potassium phosphate, pH 7.8 containing 1 mM $MgCl_2$. The mixture was centrifuged at 4000×g for 5 min between washes. The amount of protein bound to the resin was determined as described for the immobilization of the aminotransferase from *Bacillus sphaericus* described in Example 10. The washed immobilized-enzyme beads were finally suspended in 3 mL of 100 mM potassium phosphate, pH 7.8 containing 1 mM $MgCl_2$. The unreacted epoxy groups of the immobilized-enzyme beads were blocked by incubation with 1.4 M glycine at ambient temperature with gentle mixing. After 24 h, the beads were washed with 4×10 mL of 50 mM EPPS, pH 8.4 containing 1 mM $MgCl_2$ to remove the excess glycine and were finally resuspended in 5 mL of 50 mM EPPS, pH 8.4 containing 1 mM $MgCl_2$. The final concentration of immobilized enzyme was 90 mg protein per g resin bead.

Example 14

Expression of SEQ ID NO:2 Aldolase Cloned Without a Purification Tag

The gene of SEQ ID NO:1 was subcloned using standard molecular biology procedures into a derivative of the pET23d vector (Novagen, Madison, Wis.) containing the *E. coli* metE gene and promoter inserted at the NgoMIV restriction site and a second psii restriction site that was added for facile removal of the beta lactamase gene (bla). The construction of this vector containing an insert for a myo-inositol oxygenase gene is described in PCT WO 2006/066072 in Examples 2 and 20. The aldolase insert was confirmed by DNA sequencing (Agencourt Bioscience Corporation; Beverly, Mass.) and the plasmid with the correct insert sequence was transformed into the *E. coli* expression host BW30384(DE3)ΔompTΔ-metE. The construction of this expression host and the transformation protocol are also described in PCT WO 2006/066072 (Examples 21 and 22). The aldolase gene was expressed by induction with lactose in a 3 L fermentor. The protocol for the induction is described in Example 1. To prepare cell free extract containing the aldolase, the cells were suspended in 3-4 volumes of 100 mM potassium phosphate, pH 7.8, containing 1 mM $MgCl_2$ and then disrupted as described in Example 2. The cell debris was removed by centrifugation at 20,000 to 25,000×g for 30 minutes at 4° C. The soluble proteins in the cell free extracts were separated on a Bio-Rad Laboratories Experion Automated Electrophoresis Station (Bio-Rad, Hercules, Calif.) and analyzed for percent soluble protein expression using the Experion Software or by SDS polyacrylamide gel electrophoresis using 4-15% gradient gels.

Example 15

Biocatalytic Production of R,R-Monatin from D-Tryptophan and Pyruvate Using a 2-Step Reaction in a Small Fermentor Materials All reagents were of analytical grade or the highest grade commercially available. The D-alanine aminotransferase used in the biocatalytic production of R,R-monatin was purchased from Biocatalytics, Inc. (Pasadena, Calif.) (catalog # AT-103) while the SEQ ID NO:2 aldolase used in the production was prepared as described in Example 14.

Methods and Results

A 2-step reaction was carried out at 250 mL in a 0.7 L INFORS (Bottmingen, Switzerland) bioreactor. The reaction was maintained at pH 8.4 and 25° C. under a nitrogen headspace.

Mixture 1 (First Reaction mixture): A solution of 25 mM EPPS, pH 8.4, 1 mM $MgCl_2$, 5 mM potassium phosphate and 50 μM pyridoxal phosphate (PLP) was prepared in the fermentor. The liquid was sparged with nitrogen for several minutes before the additions of 200 mM sodium pyuvate and 100 mM D-tryptophan as solids. The pH was adjusted to 8.4 with sodium hydroxide after the addition of the substrates and before the addition of the enzymes. The D-alanine aminotransferase was added as a solid to a final concentration of 2 mg/mL and the aldolase was added as a cell free extract to a final concentration of 0.01 mg/mL (final volume of 250 mL after the addition of enzymes and substrates). The reaction mixture was incubated at 25° C. with agitation at 250 rpm under a nitrogen headspace. The progress of the reaction was followed by measuring D-tryptophan, D-alanine, R,R-monatin, R-monatin precursor (2-hydroxy-2-(1H-indol-3-ylmethyl)-4-oxo-pentanedioic acid) and pyruvic acid. Tryptophan and alanine concentrations were measured utilizing the fluorescence post-column derivatization method. Monatin was quantified using the LC/MS/MS method. All analytical methods are described in Example 6.

Ultrafiltration: After overnight incubation the protein was removed from the reaction mixture by ultrafiltration using a Millipore Pellicon® 50 $cm^2$ ultrafiltration cartridge (MWCO 10,000) (GE Healthcare, Piscataway, N.J.). Oxygen was excluded during the process by maintaining a nitrogen atmosphere in the original fermentor and in a second fermentor that received the permeate.

Mixture 2 (Second Reaction mixture): 2: To the deproteinized solution (approximately 230 mL) was added D-alanine to a final concentration of 1 M and the D-alanine aminotransferase to a final concentration of 2 mg/mL. The reaction was incubated at 25° C. with agitation at 250 rpm under a nitrogen headspace. The progress of the reaction was followed as described above for Mixture 1.

The results show that the 2-step process improves monatin titer over 2-fold when the process is carried out at the 250 mL scale.

Example 16

Small Scale Biocatalytic Production of R,R-Monatin from D-Tryptophan and Pyruvate Using 2 Reaction Steps and Immobilized Enzymes Materials The *B. sphaericus* $HIS_6$-tagged D-alanine aminotransferase and the $HIS_6$-tagged SEQ ID NO:2 aldolase used to catalyze the formation of R,R-monatin were immobilized as described in Examples 10 and 13. The reactions were set up and carried out in a Coy anaerobic chamber with an atmosphere of 97-98% nitrogen and 2-3% hydrogen to minimize the oxygen catalyzed degradation of the reaction intermediates.

Methods and Results

Reaction 1: A solution of 100 mM sodium pyruvate, 1 mM $MgCl_2$, and 50 μM PLP in 50 mM EPPS, pH 8.4 was prepared using degassed $H_2O$ in a Coy anaerobic chamber. To this solution was added solid D-tryptophan to a final concentration of 50 mM. Immobilized enzyme solutions were added to the reactions at 0.05 g/L for the immobilized SEQ ID NO:2 aldolase and 2 g/L for the immobilized aminotransferase (4 mL final volume). The reaction mixture was incubated at room temperature with gentle mixing. The progress of the reactions was followed by measuring D-tryptophan, D-alanine, R,R-monatin, R-monatin precursor (2-hydroxy-2-(1H-indol-3-ylmethyl)-4-oxo-pentanedioic acid) and pyruvic acid concentrations. All analytical methods are described in Example 6. For monatin, the LC/MS/MS method was utilized. For tryptophan and alanine, the fluorescence post-column derivatization method was utilized. For pyruvate analysis, the Aminex® column was utilized for the separation.

After the overnight incubation, the immobilized enzymes were removed from the reaction mixture by filtration through a 0.45 micron syringe filter.

Reaction 2: Solid D-alanine was added to the filtered material to a final concentration of 1 M and immobilized aminotransferase to a concentration of 2 g/L protein (final volume

TABLE 4

Production of R,R-monatin using a 2-step reaction to improve the monatin titer in a small fermentor

| Reaction 1 final concentrations | | | | Reaction 2 final concentrations | | | |
|---|---|---|---|---|---|---|---|
| [Monatin] mM | [Alanine] mM | [Tryptophan] mM | [Monatin Precursor] mM | [Monatin] mM | [Alanine] mM | [Tryptophan] mM | [Monatin Precursor] mM |
| 6.7 | 66.8 | 26.0 | 11.5 | 14.6 | 1374.0 | 59.4 | 4.7 | of 5.1 mL). The reaction mixture was incubated at room temperature with gentle mixing. The progress of the reactions was followed by HPLC and/or LC-MS analyses, measuring D-tryptophan, D-alanine, R,R-monatin, R-monatin precursor (2-hydroxy-2-(1H-indol-3-ylmethyl)-4-oxo-pentanedioic acid), and pyruvic acid.

TABLE 5

Small-scale production of R,R-monatin using 2 reaction steps and immobilized enzymes

| Reaction 1 final concentrations | | | | Reaction 2 final concentrations (corrected for dilution from Reaction 1) | | | |
|---|---|---|---|---|---|---|---|
| [Monatin] mM | [Alanine] mM | [Tryptophan] mM | [Monatin Precursor] mM | [Monatin] mM | [Alanine] mM | [Tryptophan] mM | [Monatin Precursor] mM |
| 4.2 | 33.8 | 15.9 | 6.2 | 9.5 | 666 | 43.9 | 0.9 |

The results show a 2-fold increase in monatin titer when a 2-step reaction process was used. By the addition of excess D-alanine and the presence of only the D-aminotransferase enzyme in the second step, approximately 5.3 mM monatin precursor was converted to monatin and approximately 28 mM indole-3-pyruvate was converted to tryptophan.

Example 17

Ultrafiltration

Materials

Three-liter quantities of reaction mixture were prepared under anaerobic conditions in 5 L Biostat B fermentors from Sartorius BBI Systems (Bethlehem, Pa.). The standard reaction contained 25 mM potassium phosphate (pH 7.8), 4 mM magnesium chloride, 0.05 mM PLP, 0.01% Tween 80, 200 mM sodium pyruvate and 100 mM L-tryptophan. To the above solution was added unpurified HEXaspC aminotransferase and purified *Comamonas testosteroni* proA aldolase at 0.5 and 0.05 g/L, respectively. The reactions were carried out under a nitrogen headspace at 30° C. and 250 rpm at pH 7.8. After 3-5 hours an additional 100 mM sodium pyruvate and 50 mM L-tryptophan were added. The reactions were stopped after 18-24 hours and held anaerobically at 4° C. prior to ultrafiltration. The ultrafiltration was operated on a SEPA CFII cross flow flat sheet membrane unit manufactured by GE Osmonics. One example of the membrane types tested was a Nadir C30 30 kDa MWCO flat sheet with a surface area of 150 cm² (Microdyn-Nadir Gmbh, Wiesbaden, Germany). Containers were designed to facilitate nitrogen flushing and blanketing to minimize the decomposition of oxygen sensitive intermediates.

Methods and Results

Analysis of monatin, alanine, tryptophan, pyruvate, I3P, and MP was conducted before and after UF operation. Monatin and tryptophan concentrations were measured using the LC-UV/Vis method described in Example 6. MP analysis was semi-quantitative, using the same LC-UV/vis method and a standard curve. Alanine was quantified using the fluorescence-based post-column derivatization method described in Example 6. Indole-3-pyruvate analysis was qualitative, based upon the peak area of indole-3-pyruvate as compared to tryptophan in Example 6. Flow rate for the UF operation was set at approximately 0.6 gpm. Backpressure on the return flow was continually adjusted to remain in the range of 50-150 psi. The concentrations of the analytes are listed in Table 6. The concentrate stream was rediluted with water to rinse the system and allow more accurate analysis.

TABLE 6

Concentration of analytes

| Description | Volume in Tank | Monatin (ppm) | Trp (ppm) | Ala (ppm) | Pyr (ppm) | MP (ppm) | I3P (ppm) |
|---|---|---|---|---|---|---|---|
| Feed, Batch 071306 | 3400 | 5742.6 | 10832.3 | 3235.0 | 2555.6 | 5461.5 | 874.1 |
| UF Permeate | 2948.4 | 5115.0 | 9946.5 | 2903.9 | 2417.7 | 5006.9 | 585.4 |
| UF concentrate | 2580.2 | 1628.2 | 2517.4 | 451.1 | 629.4 | 1330.6 | 290.8 |

The feed was concentrated 8-fold and recoveries of all components were excellent. SDS-PAGE analysis of the permeate demonstrated complete removal of protein components.

Example 18

Anion Exchange

Materials

A 43 mL packed volume of resin ZGA313 sourced from Itochu Chemicals America, Inc. in the acetate form was used for anion exchange purification of monatin. A mock solution containing tryptophan, alanine, and monatin, in ratios similar to that observed after cation exchange treatment of the bioreaction, was used as the feedstock. Reagent grade potassium acetate was used as an eluent in a 3 M solution.

Methods and Results

The solution was loaded, and rinsed with deionized water at 2.5 mL/min before eluting at the same rate. Results are listed in Table 7. A conservative single batch loading capacity was calculated to be 0.1 g of monatin per mL of packed resin. Excellent purity and recovery of monatin was observed. A small amount of monatin washed through without binding and a fraction of alanine was not completely rinsed out of the column before elution began. The analytes were measured as described in Example 17.

TABLE 7

Results

| Description | Volume | Mon (ppm) | Trp (ppm) | Ala (ppm) |
|---|---|---|---|---|
| Feed | 2494 | 1897.1 | 5816.7 | 64717.3 |
| Wash through | 2739 | 192.8 | 5832.9 | 54250.4 |
| Eluate 1, 3 M KOAc | 1016 | 4285.1 | 0 | 42.8 |

Example 19

Specialty Membrane Purification

Materials

Three L of protein free ultrafiltration permeate were used as feedstock. The pH was adjusted to 7.36 with HCl. The membrane was operated on a SEPA CFII cross flow flat sheet membrane unit manufactured by GE Osmonics. One example of the membrane types tested was named NP manufactured by ITT Aquios-PCI Membrane Systems, Inc. (Basingstoke, UK). It was tested as a flat sheet with a surface area of 150 $cm^2$. Containers were designed to facilitate nitrogen flushing and blanketing to minimize the decomposition of oxygen sensitive intermediates.

Methods and Results

Analysis of monatin, alanine, tryptophan, pyruvate, I3P, and MP was conducted at each step of the membrane operation using the methods described in Example 17. Three diafiltrations were performed after the initial concentration. Flow rate for the membrane operation was set at approximately 0.4 gpm. Backpressure on the return flow was continually adjusted to remain in the range of 100-400 psi. The concentrations of the analytes are listed in Table 8. The concentrate streams were rediluted with water to rinse the system and allow more accurate analysis.

TABLE 8

Concentration of analytes

| Description | Volume in Tank | Mon (g) | Trp (g) | Ala (g) | Pyr (g) | MP (g) | I3P (g) |
|---|---|---|---|---|---|---|---|
| Feed | 3054.8 | 12.92 | 20.34 | 5.89 | 11.79 | 26.48 | 1.79 |
| Permeate 1 | 2051.6 | 0.94 | 8.68 | 2.46 | 8.92 | 5.67 | 1.04 |
| Concentrate 1 | 3024.1 | 10.67 | 9.93 | 2.38 | 4.40 | 17.36 | 1.24 |
| Permeate 2 | 2412.5 | 0.21 | 2.81 | 1.03 | 2.14 | 1.62 | 0.22 |
| Concentrate 2 | 3046.3 | 10.27 | 7.67 | 1.66 | 3.27 | 16.79 | 1.29 |
| Permeate 3 | 2542.9 | 0.26 | 2.82 | 0.77 | 1.82 | 1.71 | 0.20 |
| Concentrate 3 | 3074.8 | 10.13 | 5.67 | 1.04 | 2.23 | 16.10 | 1.20 |
| Permeate 4 | 2658.4 | 0.38 | 3.23 | 0.69 | 1.31 | 1.86 | 0.22 |
| Concentrate 4 | 918.1 | 9.90 | 4.53 | 0.52 | 1.53 | 14.81 | 0.91 |

The NP membrane showed strong rejection of monatin and rapid washout of the smaller molecules like alanine and pyruvate. This makes it a good candidate to significantly reduce the alanine load on downstream purification options. In addition, the mild conditions are ideal for recycling of the various components while avoiding decomposition. Other promising membrane options include NF270 (Filmtec™, the Dow Chemical Company, Midland, Mich.) and NFB (ITT Aquios-PCI Membrane Systems, Inc. (Basingstoke, UK).

Example 20

SDVB Separation

Materials

Feed material consisted of a mock solution of monatin, tryptophan, alanine, and pyruvate with concentrations listed in Table 9. A synthetic, SDVB adsorbent resin HP21 manufactured by Mitsubishi was used to purify monatin from the mixture. Reagent grade ethanol and deionized water were used as eluents. The packed volume of the column was 98.7 ml with dimensions of 1.5 cm diameter by 55.9 cm height.

Methods and Results:

Absorbance at 280 nm was used to track the elution and select fractions. Flow rate was set at 2.5 ml/min. The resin was equilibrated with water adjusted to pH 8.5 with sodium hydroxide. Four fractions were collected for analysis and are listed in Table 9. The column was washed with deionized water through the first three fractions. The final fraction, containing mainly tryptophan, was eluted with 10% aqueous ethanol.

TABLE 9

Concentration of analytes

| Description | Volume | Mon (g) | Trp (g) | Ala (g) | Pyr (g) |
|---|---|---|---|---|---|
| Feed | 49.5 | 0.43 | 0.53 | 0.42 | 0.47 |
| Wash through | 48.1 | 0.00 | 0.00 | 0.00 | 0.00 |
| Frac 2 | 95.1 | 0.00 | 0.00 | 0.31 | 0.44 |
| Frac 3 | 533.4 | 0.38 | 0.00 | 0.01 | 0.00 |
| Frac 4, 10% EtOH | 603.4 | 0.01 | 0.32 | 0.00 | 0.00 |

The primary challenge is the separation of monatin from alanine in this scenario, particularly given a two-reaction scheme where excess alanine is used to drive the reaction further. Appropriate column sizing will be critical for this separation. It is possible that another, similar type of SDVB resin will offer better capacities and enhanced separation. Possibilities include SP70 or SP850 both from Mitsubishi, or others yet to be tested. The use of 10% ethanol expedites the elution of tryptophan. It may be possible to load UF permeate directly onto an SDVB column eliminating other purification steps, but the relative capacity of the column will be sacrificed.

Comparatively, use of a SDVB resin to desalt the anion resin eluent allows quite high loading rates as can be seen in Table 10.

TABLE 10

Results of desalting

| Description | Volume | Mon (g) | Salt (g) |
|---|---|---|---|
| Feed | 200 | 1.95 | 81.18 |
| Frac 1 | 410 | 0.00 | 69.80 |

TABLE 10-continued

Results of desalting

| Description | Volume | Mon (g) | Salt (g) |
|---|---|---|---|
| Frac 2 | 256 | 0.04 | 0.05 |
| Frac 3-50% EtOH | 1040 | 1.82 | 0.00 |

For the desalting use, SP70 resin from Mitsubishi was packed in a 103 mL column with dimensions of 1.5 cm by 58.4 cm. Excellent recoveries and capacities were observed. The final fraction was eluted with 50% aqueous ethanol to reduce peak tailing. Good separation from the salt allowed a very pure fraction of monatin to be collected and recovered.

Example 21

Electrodialysis

Materials

A lab scale electrodialysis unit was utilized for this test. All chemicals were reagent grade. Anolyte and catholyte were 1 M sodium bicarbonate solutions. The concentrate solution was a 0.1% sodium chloride solution. Membranes used were AMX and CMX. Electrode membranes were Nafion membranes. Feed pressure was set to less than 1 psi. The run lasted 80 minutes and was stopped when the voltage began climbing rapidly. The current was lowered to reduce the potential twice during the run. The feed pH was set to 7.4 and rose slightly to 7.7 while the concentrate pH finished at 7.2. The concentrations of the four analytes used for the feed are listed in Table 11 (measured as described in Example 17).

Methods and Results

Final analysis of the mass balance showed that pyruvate was the only molecule transported to any significant degree. The other three analytes adsorbed to the membrane during the run and were leached free during the efficiency-testing phase.

It was surmised that despite testing with the highest diffusivity membranes available, most of the molecules were too large to be transported across the membrane, monatin in particular. Several other pH's and membranes were tested with similar results. Nonetheless, the ability to selectively separate significant concentrations of pyruvate make this an interesting option in designing a downstream processing method. Since alanine is very similar in size to pyruvate, it is expected that one could find a membrane which would allow diffusion of alanine through the membrane under the appropriate conditions.

TABLE 11

| Description | Volume (mL) | Monatin (ppm) | Trp (ppm) | Ala (ppm) | Pyr (ppm) |
|---|---|---|---|---|---|
| Feed, t = 0 pH 7.4 | 235 | 4433.7 | 6337.1 | 564635.6 | 3740.5 |
| Conc, t = 0 | 505 | 0 | 0 | 0.0 | 26.7 |
| Feed, t = 20 | 245 | 4208.9 | 6166.3 | 549417.3 | 2171.1 |
| Conc, t = 20 | 495 | 0 | 0 | 0.0 | 749.9 |
| Feed, t = 50 | 255 | 4165.7 | 6431.5 | 573046.7 | 926.7 |
| Conc, t = 50 | 475 | 119.3 | 0 | 0.0 | 1343.8 |
| Final Feed | 270 | 3017.5 | 4991.137 | 444710.3 | 536.2 |
| Final Concentrate | 457 | 157.9 | 0 | 0.0 | 1649.5 |
| Feed from efficiency test | 490 | 20.5 | 26.1 | 2325.5 | 0.0 |
| Conc from efficiency test | 510 | 51.5 | 13.8 | 1229.6 | 0.0 |
| Electrolyte | 500 | 0 | 0 | 0.0 | 0.0 |

Example 22

Cation Exchange

One can imagine a method allowing the purification of monatin from the other reaction components, including other amino acids, using a strong cation exchange resin in a single step. A strong acid cation exchange resin in the acid form is the preferred resin. Deproteinized reaction mix is loaded and the organic acid compounds are washed off, leaving only the amino acids bound to the column. A step gradient is used to elute the amino acids separately on the basis of the difference in the isoelectric points. The step gradient might consist of a citric buffer or phosphate buffer, with steps at pH 2.5, 3, 3.1, and 4. Because monatin's pI is approximately 3.9 while tryptophan and alanine have a pI that is closer to 6, monatin should elute first. For example, see MCI GEL® Technical Information 2004-2005, Mitsubishi Chemical Corporation, page 7.

Example 23

Cation Exchange

Materials: 7.5 cm diameter column was packed with 950 ml packed volume of AG50Wx8 cation exchange resin in the proton form. AG50Wx8 is manufactured by Rohm and Haas (Philadelphia, Pa.) and was sourced from Bio-Rad (Hercules, Calif.). One liter of an ultrafiltered bioreaction mixture was fed to the column at a flow rate of 140 mL/min. Deionized water was used as a wash. The column was eluted using 1M potassium hydroxide.

Methods and Results: Following the loading step of one liter of feed, 44.6 liters of water were used to wash the column until the absorbance at 280 nm was reduced sufficiently. Subsequently, the column was eluted with 1M KOH for a total collected volume of 14.7 liters. Analysis of the various analytes is listed in Table 12.

TABLE 12

| Description | Volume | Monatin (g) | Tryptophan (g) | Alanine (g) | HMG (g) | Pyruvate (g) | I3P (g) | MP (g) | HMO (g) |
|---|---|---|---|---|---|---|---|---|---|
| Feed | 1000 | 5.70 | 12.00 | 3.74 | 2.02 | 1.20 | 0.85 | 14.28 | 8.71 |
| Washthrough 1 | 22450 | 0.02 | 0.17 | 0.00 | 0.22 | 4.15 | 0.22 | 10.33 | 4.49 |
| Washthrough 2 | 22150 | 0.00 | 0.00 | 0.00 | 0.18 | 0.00 | 0.00 | 2.79 | 0.00 |
| Eluate, 1M KOH | 14700 | 4.91 | 11.15 | 3.53 | 1.68 | 0.00 | 0.00 | 1.35 | 0.00 |

Additional steps could further purify components of the eluate.

Example 24

Anion Exchange

Monatin is purified from a reaction mixture, for example the one described in Example 17 for S,S-monatin, using a strong anion exchange resin in a single step. A strong anion exchange resin, such as ZGA313 (Itochu Chemicals America, Inc) in the bicarbonate form, is the preferred resin. Deproteinized reaction mixture is loaded onto an appropriately sized column at pH 7-8. The uncharged amino acids, such as alanine and tryptophan, do not bind and are washed off with water. The molecules with a negative charge at pH 7-8 are retained on the column. These include monatin, 4-hydroxy-4-methyl glutamic acid, 4-hydroxy-4-methyl-oxoglutaric acid, pyruvic acid, indole-3-pyruvic acid, and monatin precursor. At pH 7-8, using a linear salt gradient (such as ammonium bicarbonate from 0 to 2 M), monatin would be expected to elute before the organic acids (for example, pyruvic acid, 4-hydroxy-4-methyl oxoglutaric acid, monatin precursor and indole-3-pyruvic acid). Hydrophobic interactions between the indole moiety of monatin and the backbone of the resin, should retard the elution of monatin and allow selective separation of monatin from 4-hydroxy-4-methyl glutamic acid. The chromatography fractions can be analyzed using the methods described in Example 6.

Additional modifications to the described invention will be evident to those skilled in the art without departing from the spirit and scope of the invention. For example, although ultrafiltration is indicated as a preferred step in the process, other filtration processes that separate the larger molecular weight enzymes from the balance of the reaction constituents, such as gel filtration or size exclusion chromatography are also possible. And, the selection of specific enzymes and constituents can be varied among those identified herein. The specific quantities of reactants can be varied, as can the amounts recycled and the number of recycles to improve overall process efficiency.

What is claimed is:

1. A method of making monatin in vitro, the method comprising:
   a) providing D-tryptophan and pyruvate to a reactor, forming a first composition which includes monatin produced via a multi-step equilibrium pathway in which D-tryptophan is converted to indole-3-pyruvate, indole-3-pyruvate is converted to 2-hydroxy 2-(indol-3-ylmethyl)-4-keto glutarie (MP), and MP is converted to R,R-monatin;
   b) providing to the reactor a first-step polypeptide capable of facilitating the conversion of D-tryptophan to indole-3-pyruvate, wherein the first-step polypeptide is chosen from tryptophan aminotransferase (EC 2.6.1.27), tyrosine (aromatic) aminotransferase (EC 2.6.1.5), tryptophan dehydrogenase (EC 1.4.1.19), tryptophan-phenylpyruvate transaminase (EC 2.6.1.28), aspartate aminotransferase (EC 2.6.1.1), L-amino acid oxidase (EC 1.4.3.2), D-amino acid dehydrogenase (EC 1.4.99.1), D-amino acid oxidase (EC 1.4.3.3), D-amino acid (D-alanine) aminotransferase (EC 2.6.1.21), or a combination thereof;
   c) providing to the reactor a second-step polypeptide capable of facilitating the conversion of indole-3-pyruvate to MP, wherein the second-step polypeptide is chosen from 4-hydroxy-2-oxoglutarate glyoxylate-lyase (EC 4.1.3.16) and 4-hydroxy-4-methyl-2-oxoglutarate pyruvate-lyase (EC 4.1.3.17);
   d) providing to the reactor a third-step polypeptide capable of facilitating the conversion of MP to R—R-monatin, wherein the third-step polypeptide is chosen from tryptophan aminotransferase (2.6.1.27), tyrosine (aromatic) aminotransferase (2.6.1.5), tryptophan dehydrogenase (1.4.1.19), tryptophan-phenylpyruvate transaminase (EC 2.6.1.28), aspartate aminotransferase (EC 2.6.1.1), glutamate dehydrogenase (1.4.1.2-4), phenylalanine dehydrogenase (EC 1.4.1.20), D-amino acid dehydrogenase (1.4.99.1), D-amino acid (D-alanine) aminotransferase (EC 2.6.1.21), D-methionine-pyruvate aminotransferase (2.6.1.41), and combinations thereof;
   e) removing, inhibiting, inactivating or degrading the second-step polypeptide to form a second composition; and
   f) providing alanine to the second composition to drive the conversion of MP to R,R-monatin.

2. The method of claim 1 further comprising:
   providing an additional amount of the third-step polypeptide to the second composition to facilitate the conversion of MP to R,R-monatin.

3. The method of claim 1 wherein the third-step polypeptide is the same as the first polypeptide.

* * * * *